(12) United States Patent
Park et al.

(10) Patent No.: US 10,905,107 B2
(45) Date of Patent: Feb. 2, 2021

(54) TRANSGENIC MOUSE CAPABLE OF SPATIAL AND TEMPORAL CONTROL OF EXPRESSION AND SITE-SPECIFIC MODIFICATION OF TARGET PROTEIN, PRODUCTION METHOD AND USES THEREOF

(71) Applicant: KOREA ADVANCED INSTITUTE OF SCIENCE AND TECHNOLOGY, Daejeon (KR)

(72) Inventors: Hee-Sung Park, Daejeon (KR); Aerin Yang, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 564 days.

(21) Appl. No.: 15/695,417

(22) Filed: Sep. 5, 2017

(65) Prior Publication Data
US 2018/0064076 A1    Mar. 8, 2018

Related U.S. Application Data

(60) Provisional application No. 62/383,560, filed on Sep. 5, 2016.

(51) Int. Cl.
*A01K 67/027*    (2006.01)
*C12N 15/85*    (2006.01)
*C12N 9/00*    (2006.01)

(52) U.S. Cl.
CPC ............ *A01K 67/0275* (2013.01); *C12N 9/93* (2013.01); *C12N 15/8509* (2013.01);
(Continued)

(58) Field of Classification Search
None
See application file for complete search history.

(56) References Cited

FOREIGN PATENT DOCUMENTS

| KR | 1020150070186 A | 6/2015 | | |
| WO | WO 2014/044872 A1 * | 3/2014 | ............ | C12P 21/02 |
| WO | WO2017064718 A1 * | 4/2017 | ............ | G01N 33/53 |

OTHER PUBLICATIONS

De Schamphelaire et al., "Mammalian expression vector pEF1hCASP-9-His, complete sequence", ACCESSION: LT727003, Submitted: Feb. 2, 2017 (see Search Results, 20200219_113813_us-15-695-417-3.rge, Result 1). (Year: 2017).*

(Continued)

*Primary Examiner* — Kevin K Hill
*Assistant Examiner* — James Joseph Graber
(74) *Attorney, Agent, or Firm* — Hultquist, PLLC; Steven J. Hultquist

(57) ABSTRACT

The present invention relates to a mouse (*Mus musculus*) in which expression and site-specific modification of a target protein is temporally and spatially controlled, and a method for producing the same and the use thereof, and more particularly to a transgenic mouse in which expression of a target protein having a modification attached to a specific position is temporally and spatially controlled as a result of incorporation of an unnatural amino acid. In the mouse according to the present invention, in which site-specific modification of a target protein is temporally and spatially controllable, expression of the target protein having the site-specific modification attached thereto is controllable depending on the timing and/or position of introduction of an unnatural amino acid. Thus, the mouse according to the present invention is useful for studies on the in vivo functions of cellular proteins, various human diseases including cancers and neurodegenerative disorders, new drug discovery, and the like.

11 Claims, 22 Drawing Sheets
(12 of 22 Drawing Sheet(s) Filed in Color)
Specification includes a Sequence Listing.

(52) U.S. Cl.
CPC ............. *C12Y 601/01006* (2013.01); *A01K 2217/072* (2013.01); *A01K 2217/15* (2013.01); *A01K 2217/20* (2013.01); *A01K 2217/206* (2013.01); *A01K 2227/105* (2013.01); *A01K 2267/03* (2013.01)

(56) References Cited

OTHER PUBLICATIONS

Lee, S., "Expanding the Genetic Code of a Mouse", Dissertation Submitted to the Graduate School of Ajou University, Jul. 2015, pp. i-iv and 1-22. (Year: 2015).*

Ernst, et al. "Genetic code expansion in the mouse brain", Nature Chemical Biology, vol. 12, Oct. 2016 (Published online: Aug. 2016). (Year: 2016).*

Elliott, et al., "Proteome labeling and protein identification in specific tissues and at specific developmental stages in an animal", Nature Biotechnology, vol. 32, No. 5, May 2014. (Year: 2014).*

Choudhary, C., et al, "The growing landscape of lysine acetylation links metabolism and cell signalling", "Nature Reviews", Aug. 2014, pp. 536-550, vol. 15.

Gordon, J. W., et al., "Integration and Stable Germ Line Transmission of Genes Injected into Mouse Pronuclei", "Science", Dec. 11, 1981, pp. 1244-1246, vol. 214, No. 4526.

Liu, C. C., et al., "Adding New Chemistries to the Genetic Code", "Annual Review of Biochemistry", Mar. 18, 2010, pp. 413-414, vol. 79.

Rosenthal, N., et al., "The mouse ascending: perspectives for human-disease models", "Nature Cell Biology", Sep. 2007, pp. 993-999, vol. 9, No. 9.

Schvartzman, J.-M., et al., "Mitotic chromosomal instability and cancer: mouse modelling of the human disease", "Nature Reviews Cancer", Feb. 2010, pp. 102-115, vol. 10, No. 2.

Terzioglu, M., et al., "MTERF1 Binds mtDNA to Prevent Transcriptional Interference at the Light-Strand Promoter but is Dispensable for rRNA Gene Transcription Regulation", "Cell Metabolism", Apr. 2, 2013, pp. 618-626, vol. 17.

Umehara, T., et al., "N-Acetyl lysyl-tRNA synthetases evolved by a CcdB-based selection possess N-acetyl lysine specificity in vitro and in vivo", "FEBS Letters", Jan. 28, 2012, pp. 729-733, vol. 586.

Walsh, C. T., et al., "Protein Posttranslational Modifications: The Chemistry of Proteome Diversifications", "Angewandte Chemie International Edition", Dec. 1, 2005, pp. 7342-7372, vol. 44, No. 45.

Yang, A., et al., "A chemical biology route to site-specific authentic protein modifications", "Science", Nov. 4, 2016, pp. 623-626, vol. 354, No. 6312.

Lee, S., "Expanding the Genetic Code of a Mouse", "Dissertation Submitted to the Graduate School of Ajou University", Jul. 2015, pp. 1-29.

Xia, X.G., et al., "An Enhanced U6 Promoter for Synthesis of Short Hairpin RNA", "Nucleic Acids Research", 2003, pp. 1-5, vol. 31, No. 17.

* cited by examiner

| Residues | Peptide sequence | Expected mass [M+H]+ | Measured mass [M+H]+ | | | | |
|---|---|---|---|---|---|---|---|
| | | | Wt(39Y) | 39AcK | 39TfAcK | 39BrF | |
| 1-4 | MASK | 436.2 | | | | | |
| 5-27 | QEELFTGVVPILVELDGDVNGHK | 2437.3 | 2437.4 | 2437.7 | 2437.1 | 2437.8 | |
| 20-42 | FSVSGEGEGDATYGK | 1503.7 | 1503.7 | 1510.9 | 1564.6 | 1565.8 | |
| 43-74 | LTLKFICTTGKLPVPWPTLVTTFSYGVQCFSR | 3603.9 | 3601.7 | 3602.1 | 3601.1 | 3602.1 | |
| 75-80 | YPDHMK | 790.4 | ND | 790.5 | 790.3 | 790.5 | |
| 75-91 | YPDHMKR | 946.5 | 946.5 | 946.6 | 946.4 | 946.6 | |
| 81-86 | RHDFFK | 849.4 | 849.5 | 849.8 | 849.4 | 849.6 | |
| 82-86 | HDFFK | 693.3 | 693.4 | 693.5 | 693.3 | 693.5 | |
| 87-97 | SAMPEGYVQER | 1266.6 | 1266.6 | 1266.8 | 1266.6 | 1266.8 | |
| 98-102 | TISFK | 595.3 | ND | 595.5 | 595.3 | ND | |
| 98-108 | TISFKDDGNYK | 1287.6 | 1287.7 | 1287.8 | 1287.6 | 1287.8 | |
| 98-110 | TISFKDDGNYKTR | 1544.8 | 1544.9 | 1545.0 | 1544.7 | 1545.1 | |
| 111-123 | AEVKFEGDTLVNR | 1477.8 | 1477.8 | 1478.0 | 1477.7 | 1478.0 | |
| 111-127 | AEVKFEGDTLVNRIELK | 1961.1 | 1961.1 | 1961.4 | 1961.0 | 1961.5 | |
| 115-123 | FEGDTLVNR | 1050.5 | 1050.5 | 1050.7 | 1060.5 | 1060.7 | |
| 115-127 | FEGDTLVNRIELK | 1533.8 | 1533.9 | 1534.1 | 1533.8 | 1534.1 | |
| 128-132 | GIDFK | 579.9 | ND | 579.4 | 579.3 | ND | |
| 128-141 | GIDFKEDGNILGHK | 1542.8 | 1542.9 | 1543.0 | 1542.8 | 1543.1 | |
| 128-157 | GIDFKEDGNILGHKLEYNYN SHNVYITADK | 3467.7 | 3468.8 | 3468.2 | 3467.2 | 3468.2 | |
| 128-159 | GIDFKEDGNILGHKLEYNYNSHNVYITADKQK | 3723.8 | 3724.1 | 3724.5 | 3723.2 | 3724.4 | |
| 142-159 | LEYNYNSHNVYITADKQK | 2200.1 | 2200.1 | 2200.4 | 2199.9 | 2200.3 | |
| 160-163 | NGIK | 431.3 | | | | | |
| 164-167 | ANFK | 479.3 | | | | | |
| 168-210 | IRHNIEDGSVQLADHYQQNT PIGDGPVLLPDNHYLSTQSA LSK | 4741.4 | 4741.4 | 4742.3 | 4740.3 | 4742.4 | |
| 170-210 | IRHNIEDGSVQLADHYQQNTPIGDGPVLLPDNHYLSTQSALSK | 4472.2 | 4472.0 | 4472.5 | 4470.8 | 4472.5 | |
| 211-215 | DPNEK | 602.3 | ND | ND | ND | ND | |
| 211-216 | DPNEKR | 758.4 | 758.4 | 758.5 | 758.4 | 758.5 | |
| 216-216 | R | 175.1 | | | | | |
| 217-239 | DHMVLLEFVTAAGITHGMDE LYK | 2590.3 | 2590.4 | 2590.6 | 2590.1 | 2590.8 | |
| 217-247 | DHMVLLEFVTAAGITHGMDELYKDYKDDDDK | 3584.7 | 3584.8 | 3586.3 | 3584.2 | 3585.3 | |
| 243-247 | DDDDK | 607.2 | 607.3 | ND | ND | 607.3 | |

FIG. 2 (cont'd.)

AcKRS cDNA

ATGTATCCATATGATGTTCCAGATTATGCTATGGATAAAAAACCACTAAACACTCTGATATCCGCAACCGGG
CTCTGGATGTCCAGGACCGGAACAATTCATAAAATAAAACACCACGAAGTCTCTCGAAGCAAAATCTATATT
GAATGGCATGCGGAGGCCACCTTGTTGTAAACAACTCCAGGAGCAGCAGGACTGCAAGAGCGCTCAGGCAC
CACAAATACAGGAAGACCTGCAAACGCTGCAGGGTTTCGGATGAGGATCTCAATAAGTTCCTCACAAAGGCA
AACGAAGACCAGACAAGCGTAAAGTCAAGGTCGTTTCTGCCCCTACCAGAACGAAAAAGGCAATGCCAAAA
TCCGTTGCGAGAGCCCCGAAACCTCTTGAGAATACAGAAGCGGCACAGGCTCAACCTTCTGGATCTAAATTT
TCACCTGCGATACCGGTTTCCACCCAAGAGTCAGTTTCTGTCCCGGCATCTGTTTCAACATCAATATCAAGC
ATTTCTACAGGAGCAACTGCATCGGCACTGGTAAAAGGGAATACGAATCCCATTACATCCATGTCTGCCCCT
GTTCAGGCAAGTGCCCCCGCACTTACGAAGAACCAGACTGACAGGCTTGAAGTCCTGTTAAACCCAAAAGAT
GAGATTCCCTGAATTCCGGCAAGCCTTTCAGGGAGCTTGAGTCCGAATTGCTCTCTCGCAGAAAAAAGAC
CTGCAGCAGATCTACGCGGAAGAAAGGGAGAATTATCTGGGGAAACTCGAGCGTGAAATTACCAGGTTCTTT
GTGGACAGGGTTTTCTGGAAATAAAATCCCCGATCCTGATCCCTCTTGAGTATATCGAAGGATGGGCATT
GATAATGATACCGAACTTTCAAAACAGATCTTCAGGGTTGACAAGAACTTCTGCCTGAGACCCATGATGGCT
CCAAACCTTCTGAACTACGCGCGCAAGCTTGACAGGCCCCTGCCTGTCCAATAAAAATTTTTGAAATAGGC

AcKRS primer1 —————————

CCATGCTACAGAAAGAGTCCGACGGCAAAGAACACTTCGAAGAGTTTACCATGCTGAACTTCTTCCAGATG
————→

GGATCGGGATGCACACGGGAAAATCTTGAAAGCATAATTACGGACTTCCTGAACCACCTGGGAATTGATTTC
AAGATCGTAGGCGATTCCTGCATGGTCTATGGGGATACCCTTGATGTAATGCACGGAGACCTGGAACTTTCC
TCTGCAGTAGTCGGACCCATACCGGTTGACCGGGAATGGGGTATTGTAAACCCTGGATAGGGGCAGGTTTC
GGGCTCGAACGCCTTCTAAAGGTTAAACACGACTTTAAAAATATCAAGAGAGCTGCAAGGTCCGAGTCTTAC
TATAACGGATTTCTACCAACCTGTGAGCGGCCGCTCGAGCATGCATCTAGAGGGCCCTATTCTATAGTGTC
ACCTAAATGCTAGAGCTCGCTGATCAGCCTCGACTGTGCCTTCTAGTTGCCAGCCATCTGTTGTTTGCCCCT

AcKRS primer2 ←—————————

CCCCCGTG

FIG. 5A

GFPamber cDNA

```
GATCTGTCCCGTTGATTTTGGTGCCAAAACAAACTCCCATTGACGTCAATGGGTGGAGACTTGGAAATCCC
     GFPamber primer1  ———————————▶
GGTGAGTCAAACCGCTATCCACGCCCATTGATGTACTGCCAAAACCGCATCACCATGGTAATAGCGATGACT
AATACGTAGATGTACTGCCAAGTAGGAAAGTCCCATAAGGTCATGTACTGGGCATAATGCCAGGCGGGCCAT
TTACCGTCATTGACGTCAATAGGGGGCGTACTTGGCATATGATACACTTGATGTACTGCCAAGTGGGCAGTT
TACCGTAAATACTCCACCCATTGACGTCAATGGAAAGTCCCTATTGGCGTTACTATGGGAACATACGTCATT
ATTGACGTCAATGGGCGGGGGTCGTTGGGCGGTCAGCCAGGCGGGCCATTTACCGTAAGTTATGTAACGCGG
AACTCCATATATGGGCTATGAACTAATGACCCCGTAATTGATTACTATTAATAACTAGGATCCAAGCTACAA
                                                GFPamber primer2  ◀———
CAAGGCAAGGCTTGACCGAGAATTCCGTGAGGCTCCGGTGCCCGTCAGTGGGCAGAGCGCACATCGCCCACA
———————————————————————
GTCCCCGAGAAGTTGGGGGGAGGGGTCGGCAATTGAACCGGTGCCTAGAGAAGGTGGCGCGGGGTAAACTGG
GAAAGTGATGTCGTGTACTGGCTCCGCCTTTTTCCCGAGGGTGGGGGAGAACCGTATATAAGTGCAGTAGTC
GCCGTGAACGTTCTTTTTCGCAACGGGTTTGCCGCCAGAACACAGGTAAGTGCCGTGTGTGGTTCCCGCGGG
CCTGGCCTCTTACGGGTTATGGCCCTTGCGTGCCTTGAATTACTTCCACCTGGCTCCAGTACGTGATTCTT
GATCCCGAGCTGGAGCCAGGGGCGGGCCTTGCGCTTTAGGAGCCCCTTCGCCTCGTGCTTGAGTTGAGGCCT
GGCCTGGGCGCTGGGGCCGCCGCGTGCGAATCTGGTGGCACCTTCGCGCCTGTCTCGCTGCTTTCGATAAGT
CTCTAGCCATTTAAAATTTTTGATGACCTGCTGCGACGCTTTTTTTCTGGCAAGATAGTCTTGTAAATGCGG
GCCAGGATCTGCACACTGGTATTTCGGTTTTTGGGGCCGCGGGCGGCGACGGGGCCCGTGCGTCCCAGCGCA
CATGTTCGGCGAGGCGGGCCTGCGAGCGCGGCCACCGAGAATCGGCGGGGGTAGTCTCAAGCTGGCCGGC
CTGCTCTGGTGCCTGGCCTCGCGACGGCCGTGTATCGCCCCGCCCTGGGCGGCAAGGCTGGCCCGGTCGGCAC
CAGTTGCGTGAGCGGAAAGATGGCCGCTTCCCGGCCCTGCTCCAGGGGCTCAAAATGGAGGACGCGGTCGT
CGGGAGAGCGGGGGGTGAGTCACCCACACAAAGGAAAGGGGCCTTTCCGTCCTCAGCCGTCGCTTCATGTG
ACTCCACGGAGTACCGGGCGCCGTCCAGGCACCTCGATTAGTTCTGGAGCTTTTGGAGTACGTCGTCTTTAG
GTTGGGGGAGGGGTTTTATGCGATGGAGTTTCCCCACACTGAGTGGGTGGAGACTGAAGTTAGGCCAGCTT
GGCACTTGATGTAATTCTCCTTGGATTTGCCCTTTTTGAGTTTGGATCTTGGTTCATTCTCAAGCCTCAGA
```

FIG. 5B

SEQUENCE LISTING

<160> NUMBER OF SEQ ID NOS: 47

<210> SEQ ID NO 1
<211> LENGTH: 464
<212> TYPE: PRT
<213> ORGANISM: Artificial Sequence
<220> FEATURE:
<223> OTHER INFORMATION: HA-AcKRS

<400> SEQUENCE: 1

```
Met Tyr Pro Tyr Asp Val Pro Asp Tyr Ala Met Asp Lys Lys Pro Leu
1               5                   10                  15

Asn Thr Leu Ile Ser Ala Thr Gly Leu Trp Met Ser Arg Thr Gly Thr
            20                  25                  30

Ile His Lys Ile Lys His His Glu Val Ser Arg Ser Lys Ile Tyr Ile
        35                  40                  45

Glu Met Ala Cys Gly Gly His Leu Val Val Asn Asn Ser Arg Ser Ser
    50                  55                  60

Arg Thr Ala Arg Ala Leu Arg His His Lys Tyr Arg Lys Thr Cys Lys
65                  70                  75                  80

Arg Cys Arg Val Ser Asp Glu Asp Leu Asn Lys Phe Leu Thr Lys Ala
                85                  90                  95

Asn Glu Asp Gln Thr Ser Val Lys Val Lys Val Val Ser Ala Pro Thr
            100                 105                 110

Arg Thr Lys Lys Ala Met Pro Lys Ser Val Ala Arg Ala Pro Lys Pro
        115                 120                 125

Leu Glu Asn Thr Glu Ala Ala Gln Ala Gln Pro Ser Gly Ser Lys Phe
    130                 135                 140

Ser Pro Ala Ile Pro Val Ser Thr Gln Glu Ser Val Ser Val Pro Ala
145                 150                 155                 160

Ser Val Ser Thr Ser Ile Ser Ser Ile Ser Thr Gly Ala Thr Ala Ser
                165                 170                 175

Ala Leu Val Lys Gly Asn Thr Asn Pro Ile Thr Ser Met Ser Ala Pro
            180                 185                 190

Val Gln Ala Ser Ala Pro Ala Leu Thr Lys Asn Gln Thr Asp Arg Leu
        195                 200                 205

Glu Val Leu Leu Asn Pro Lys Asp Glu Ile Ser Leu Asn Ser Gly Lys
    210                 215                 220
```

```
Pro Phe Arg Glu Leu Glu Ser Glu Leu Leu Ser Arg Arg Lys Lys Asp
225                 230                 235                 240

Leu Gln Gln Ile Tyr Ala Glu Glu Arg Glu Asn Tyr Leu Gly Lys Leu
            245                 250                 255

Glu Arg Glu Ile Thr Arg Phe Phe Val Asp Arg Gly Phe Leu Glu Ile
        260                 265                 270

Lys Ser Pro Ile Leu Ile Pro Leu Glu Tyr Ile Glu Arg Met Gly Ile
    275                 280                 285

Asp Asn Asp Thr Glu Leu Ser Lys Gln Ile Phe Arg Val Asp Lys Asn
290                 295                 300

Phe Cys Leu Arg Pro Met Met Ala Pro Asn Leu Leu Asn Tyr Ala Arg
305                 310                 315                 320

Lys Leu Asp Arg Ala Leu Pro Asp Pro Ile Lys Ile Phe Glu Ile Gly
            325                 330                 335

Pro Cys Tyr Arg Lys Glu Ser Asp Gly Lys Glu His Leu Glu Glu Phe
        340                 345                 350

Thr Met Leu Asn Phe Phe Gln Met Gly Ser Gly Cys Thr Arg Glu Asn
    355                 360                 365

Leu Glu Ser Ile Ile Thr Asp Phe Leu Asn His Leu Gly Ile Asp Phe
370                 375                 380

Lys Ile Val Gly Asp Ser Cys Met Val Tyr Gly Asp Thr Leu Asp Val
385                 390                 395                 400

Met His Gly Asp Leu Glu Leu Ser Ser Ala Val Val Gly Pro Ile Pro
            405                 410                 415

Leu Asp Arg Glu Trp Gly Ile Asp Lys Pro Trp Ile Gly Ala Gly Phe
        420                 425                 430

Gly Leu Glu Arg Leu Leu Lys Val Lys His Asp Phe Lys Asn Ile Lys
    435                 440                 445

Arg Ala Ala Arg Ser Glu Ser Tyr Tyr Asn Gly Ile Ser Thr Asn Leu
450                 455                 460

<210> SEQ ID NO 2
<211> LENGTH: 69
<212> TYPE: DNA
<213> ORGANISM: Artificial Sequence
<220> FEATURE:
<223> OTHER INFORMATION: tRNApyl

<400> SEQUENCE: 2
ggaaacctga tcatgtagat cgaatggact ctaaatccgt tcagccgggt tagattcccg     60
gggtttccg                                                            69

<210> SEQ ID NO 3
<211> LENGTH: 8066
<212> TYPE: DNA
<213> ORGANISM: Artificial Sequence
<220> FEATURE:
<223> OTHER INFORMATION: pAcKRS-tRNA

<400> SEQUENCE: 3
gacggatcgg gagatctccc gatcccctat ggtcgactct cagtacaatc tgctctgatg     60
ccgcatagtt aagccagtat ctgctccctg cttgtgtgtt ggcgcgccaa aaaccgcact    120
tgtccggaaa ccccgggaat ctaacccggc tgaacggatt tagagtccat tcgatctaca    180
tgatcaggtt tccctcgagt ctagaagatc tcggtgtttc gtcctttcca caagatatat    240
aaagccaaga aatcgaaata ctttcaagtt acggtaagca tatgatagtc cattttaaaa    300
```

```
cataatttta aaactgcaaa ctacccaaga aattattact ttctacgtca cgtatttgt      360 actaatatct ttgtgtttac agtcaaatta attctaatta tctctctaac agccttgtat    420
cgtatatgca aatatgaagg aatcatggga ataggccct cttcctgccc agatctgtcc     480
cgttgatttt ggtgccaaaa caaactccca ttgacgtcaa tggggtggag acttggaaat    540
ccccgtgagt caaaccgcta tccacgccca ttgatgtact gccaaaaccg catcaccatg    600
gtaatagcga tgactaatac gtagatgtac tgccaagtag gaaagtccca taaggtcatg    660
tactgggcat aatgccaggc gggccattta ccgtcattga cgtcaatagg ggcgtactt     720 ggcatatgat acacttgatg tactgccaag tgggcagttt accgtaaata ctccacccat    780
tgacgtcaat ggaaagtccc tattggcgtt actatgggaa catacgtcat tattgacgtc    840
aatgggcggg ggtcgttggg cggtcagcca ggcgggccat ttaccgtaag ttatgtaacg    900
cggaactcca tatatgggct atgaactaat gaccccgtaa ttgattacta ttaataacta    960
ggatccaagc tacaacaagg caaggcttga ccgagaattc cgtgaggctc cggtgcccgt   1020
cagtgggcag agcgcacatc gcccacagtc cccgagaagt tggggggagg ggtcggcaat   1080
tgaaccggtg cctagagaag gtggcgcggg gtaaactggg aaagtgatgt cgtgtactgg   1140
ctccgccttt ttcccgaggg tggggagaa ccgtatataa gtgcagtagt cgccgtgaac    1200 gttcttttc gcaacgggtt tgccgccaga acacaggtaa gtgccgtgtg tggttcccgc    1260
gggcctggcc tctttacggg ttatggccct tgcgtgcctt gaattacttc cacctggctc    1320
cagtacgtga ttcttgatcc cgagctggag ccaggggcgg gccttgcgct ttaggagccc    1380
cttcgcctcg tgcttgagtt gaggcctggc ctgggcgctg gggccgccgc gtgcgaatct    1440
ggtggcacct tcgcgcctgt ctcgctgctt tcgataagtc tctagccatt taaaatttt    1500 gatgacctgc tgcgacgctt tttttctggc aagatagtct tgtaaatgcg ggccaggatc    1560
tgcacactgg tatttcggtt tttggggccg cgggcggcga cggggcccgt gcgtcccagc    1620
gcacatgttc ggcgaggcgg ggcctgcgag cgcggccacc gagaatcgga cggggggtagt    1680 ctcaagctgg ccggcctgct ctggtgcctg gcctcgcgcc gccgtgtatc gccccgccct    1740
gggcggcaag gctggcccgg tcggcaccag ttgcgtgagc ggaaagatgg ccgcttcccg    1800
gccctgctcc agggggctca aaatggagga cgcggcgctc gggagagcgg gcgggtgagt    1860
cacccacaca aaggaaaggg ccttttccgt cctcagccgt cgcttcatgt gactccacgg    1920
agtaccgggc gccgtccagg cacctcgatt agttctggag cttttggagt acgtcgtctt    1980
taggttgggg ggagggggttt tatgcgatgg agtttcccca cactgagtgg gtggagactg    2040
aagttaggcc agcttggcac ttgatgtaat tctccttgga atttgccctt tttgagtttg    2100
gatcttggtt cattctcaag cctcagacag tggttcaaag ttttttttctt ccatttcagg    2160 tgtcgtgaac accggggggta ccgccaccat gtatccatat gatgttccag attatgctat    2220
ggataaaaaa ccactaaaca ctctgatatc cgcaaccggg ctctggatgt ccaggaccgg    2280
aacaattcat aaaataaaac accacgaagt ctctcgaagc aaaatctata ttgaaatggc    2340
atgcggaggc caccttgttg taaacaactc caggagcagc aggactgcaa gagcgctcag    2400
gcaccacaaa tacaggaaga cctgcaaacg ctgcagggtt tcggatgagg atctcaataa    2460
gttcctcaca aaggcaaacg aagaccagac aagcgtaaaa gtcaaggtcg tttctgcccc    2520
taccagaacg aaaaggcaa tgccaaaatc cgttgcgaga gccccgaaac ctcttgagaa    2580
tacagaagcg gcacaggctc aaccttctgg atctaaattt tcacctgcga taccggtttc    2640
cacccaagag tcagtttctg tcccggcatc tgtttcaaca tcaatatcaa gcatttctac    2700
```

```
aggagcaact gcatccgcac tggtaaaagg gaatacgaat cccattacat ccatgtctgc   2760
ccctgttcag gcaagtgccc ccgcacttac gaagaaccag actgacaggc ttgaagtcct   2820
gttaaaccca aaagatgaga tttccctgaa ttccggcaag cctttcaggg agcttgagtc   2880
cgaattgctc tctcgcagaa aaaaagacct gcagcagatc tacgcggaag aaagggagaa   2940
ttatctgggg aaactcgagc gtgaaattac caggttcttt gtggacaggg gttttctgga   3000
aataaaatcc ccgatcctga tccctcttga gtatatcgaa aggatgggca ttgataatga   3060
taccgaactt tcaaaacaga tcttcagggt tgacaagaac ttctgcctga gacccatgat   3120
ggctccaaac cttctgaact acgcgcgcaa gcttgacagg gccctgcctg atccaataaa   3180 aattttgaa ataggcccat gctacagaaa agagtccgac ggcaaagaac acctcgaaga   3240
gtttaccatg ctgaacttct tccagatggg atcgggatgc acagggaaa atcttgaaag   3300 cataattacg gacttcctga accacctggg aattgatttc aagatcgtag gcgattcctg   3360
catggtctat ggggataccc ttgatgtaat gcacggagac ctggaacttt cctctgcagt   3420
agtcggaccc ataccgcttg accgggaatg gggtattgat aaaccctgga taggggcagg   3480
tttcgggctc gaacgccttc taaaggttaa acacgacttt aaaaatatca agagagctgc   3540
aaggtccgag tcttactata acgggatttc taccaacctg tgagcggccg ctcgagcatg   3600
catctagagg gccctattct atagtgtcac ctaaatgcta gagctcgctg atcagcctcg   3660
actgtgcctt ctagttgcca gccatctgtt gtttgcccct ccccgtgcc ttccttgacc   3720 ctggaaggtg ccactcccac tgtcctttcc taataaaatg aggaaattgc atcgcattgt   3780
ctgagtaggt gtcattctat tctgggggt ggggtgggc aggacagcaa gggggaggat   3840
tgggaagaca atagcaggca tgctggggat gcggtgggct ctatggcttc tgaggcggaa   3900
agaaccagct ggggctctag ggggtatccc cacgcgccct gtagcggcgc attaagcgcg   3960
gcgggtgtgg tggttacgcg cagcgtgacc gctacacttg ccagcgccct agcgcccgct   4020
cctttcgctt tcttcccttc ctttctcgcc acgttcgccg gctttccccg tcaagctcta   4080
aatcggggca tccctttagg gttccgattt agtgctttac ggcacctcga ccccaaaaaa   4140
cttgattagg gtgatggttc acgtagtggg ccatcgccct gatagacggt ttttcgccct   4200
ttgacgttgg agtccacgtt ctttaatagt ggactcttgt tccaaactgg aacaacactc   4260
aaccctatct cggtctattc ttttgattta agggattt tggggatttc ggcctattgg   4320
ttaaaaaatg agctgattta acaaaaattt aacgcgaatt aattctgtgg aatgtgtgtc   4380
agttagggtg tggaaagtcc ccaggctccc caggcaggca gaagtatgca aagcatgcat   4440
ctcaattagt cagcaaccag gtgtggaaag tccccaggct ccccagcagg cagaagtatg   4500
caaagcatgc atctcaatta gtcagcaacc atagtcccgc ccctaactcc gcccatcccg   4560
cccctaactc cgcccagttc cgcccattct ccgccccatg ctgactaat ttttttatt   4620 tatgcagagg ccgaggccgc ctctgcctct gagctattcc agaagtagtg aggaggcttt   4680
tttggaggcc taggcttttg caaaaagctc ccgggagctt gtatatccat tttcggatct   4740
gatcaagaga caggatgagg atcgtttcgc atgattgaac aagatggatt gcacgcaggt   4800
tctccggccg cttgggtgga gaggctattc ggctatgact gggcacaaca gacaatcggc   4860
tgctctgatg ccgccgtgtt ccggctgtca gcgcaggggc gcccggttct ttttgtcaag   4920
accgacctgt ccggtgccct gaatgaactg caggacgagg cagcgcggct atcgtggctg   4980
gccacgacgg gcgttccttg cgcagctgtg ctcgacgttg tcactgaagc gggaagggac   5040
```

```
tggctgctat tgggcgaagt gccggggcag gatctcctgt catctcacct tgctcctgcc      5100
gagaaagtat ccatcatggc tgatgcaatg cggcggctgc atacgcttga tccggctacc      5160
tgcccattcg accaccaagc gaaacatcgc atcgagcgag cacgtactcg gatggaagcc      5220
ggtcttgtcg atcaggatga tctggacgaa gagcatcagg ggctcgcgcc agccgaactg      5280
ttcgccaggc tcaaggcgcg catgcccgac ggcgaggatc tcgtcgtgac ccatggcgat      5340
gcctgcttgc cgaatatcat ggtggaaaat ggccgctttt ctggattcat cgactgtggc      5400
cggctgggtg tggcggaccg ctatcaggac atagcgttgg ctacccgtga tattgctgaa      5460
gagcttggcg gcgaatgggc tgaccgcttc ctcgtgcttt acggtatcgc cgctcccgat      5520
tcgcagcgca tcgccttcta tcgccttctt gacgagttct tctgagcggg actctggggt      5580
tcgaaatgac cgaccaagcg acgcccaacc tgccatcacg agatttcgat tccaccgccg      5640
ccttctatga aaggttgggc ttcggaatcg ttttccggga cgccggctgg atgatcctcc      5700
agcgcgggga tctcatgctg gagttcttcg cccacccccaa cttgtttatt gcagcttata      5760
atggttacaa ataaagcaat agcatcacaa atttcacaaa taaagcattt ttttcactgc      5820
attctagttg tggtttgtcc aaactcatca atgtatctta tcatgtctgt ataccgtcga      5880
cctctagcta gagcttggcg taatcatggt catagctgtt cctgtgtga aattgttatc      5940 cgctcacaat tccacacaac atacgagccg gaagcataaa gtgtaaagcc tggggtgcct      6000
aatgagtgag ctaactcaca ttaattgcgt tgcgctcact gcccgctttc cagtcgggaa      6060
acctgtcgtg ccagctgcat taatgaatcg gccaacgcgc ggggagaggc ggtttgcgta      6120
ttgggcgctc ttccgcttcc tcgctcactg actcgctgcg ctcggtcgtt cggctgcggc      6180
gagcggtatc agctcactca aaggcggtaa tacggttatc cacagaatca ggggataacg      6240
caggaaagaa catgtgagca aaaggccagc aaaaggccag gaaccgtaaa aaggccgcgt      6300
tgctggcgtt tttccatagg ctccgccccc ctgacgagca tcacaaaaat cgacgctcaa      6360
gtcagaggtg gcgaaacccg acaggactat aaagatacca ggcgtttccc cctggaagct      6420
ccctcgtgcg ctctcctgtt ccgaccctgc cgcttaccgg atacctgtcc gcctttctcc      6480
cttcgggaag cgtggcgctt tctcaatgct cacgctgtag gtatctcagt tcggtgtagg      6540
tcgttcgctc caagctgggc tgtgtgcacg aaccccccgt tcagcccgac cgctgcgcct      6600
tatccggtaa ctatcgtctt gagtccaacc cggtaagaca cgacttatcg ccactggcag      6660
cagccactgg taacaggatt agcagagcga ggtatgtagg cggtgctaca gagttcttga      6720
agtggtggcc taactacggc tacactagaa ggacagtatt tggtatctgc gctctgctga      6780
agccagttac cttcggaaaa agagttggta gctcttgatc cggcaaacaa accaccgctg      6840
gtagcggtgg tttttttgtt tgcaagcagc agattacgcg cagaaaaaaa ggatctcaag      6900
aagatccttt gatcttttct acggggtctg acgctcagtg gaacgaaaac tcacgttaag      6960
ggattttggt catgagatta tcaaaaagga tcttcaccta gatcctttta aattaaaaat      7020
gaagttttaa atcaatctaa agtatatatg agtaaacttg gtctgacagt taccaatgct      7080
taatcagtga ggcacctatc tcagcgatct gtctatttcg ttcatccata gttgcctgac      7140
tccccgtcgt gtagataact acgatacggg agggcttacc atctggcccc agtgctgcaa      7200
tgataccgcg agacccacgc tcaccggctc cagatttatc agcaataaac cagccagccg      7260
gaagggccga gcgcagaagt ggtcctgcaa ctttatccgc ctccatccag tctattaatt      7320
gttgccggga agctagagta agtagttcgc cagttaatag tttgcgcaac gttgttgcca      7380
ttgctacagg catcgtggtg tcacgctcgt cgtttggtat ggcttcattc agctccggtt      7440
```

```
cccaacgatc aaggcgagtt acatgatccc ccatgttgtg caaaaaagcg gttagctcct    7500
tcggtcctcc gatcgttgtc agaagtaagt tggccgcagt gttatcactc atggttatgg    7560
cagcactgca taattctctt actgtcatgc catccgtaag atgctttct gtgactggtg     7620 agtactcaac caagtcattc tgagaatagt gtatgcggcg accgagttgc tcttgcccgg    7680
cgtcaatacg ggataatacc gcgccacata gcagaacttt aaaagtgctc atcattggaa    7740
aacgttcttc ggggcgaaaa ctctcaagga tcttaccgct gttgagatcc agttcgatgt    7800
aacccactcg tgcacccaac tgatcttcag catctttac tttcaccagc gtttctgggt     7860
gagcaaaaac aggaaggcaa aatgccgcaa aaaagggaat aagggcgaca cggaaatgtt    7920
gaatactcat actcttcctt tttcaatatt attgaagcat ttatcagggt tattgtctca    7980
tgagcggata catatttgaa tgtatttaga aaaataaaca aatagggggtt ccgcgcacat   8040 ttccccgaaa agtgccacct gacgtc                                        8066
```

<210> SEQ ID NO 4
<211> LENGTH: 21
<212> TYPE: DNA
<213> ORGANISM: Artificial Sequence
<220> FEATURE:
<223> OTHER INFORMATION: AcKRS_F

<400> SEQUENCE: 4
cgaagaccag acaagcgtaa a                                             21

<210> SEQ ID NO 5
<211> LENGTH: 22
<212> TYPE: DNA
<213> ORGANISM: Artificial Sequence
<220> FEATURE:
<223> OTHER INFORMATION: AcKRS_R

<400> SEQUENCE: 5
cttgagtccg aattgctctc tc                                            22

<210> SEQ ID NO 6
<211> LENGTH: 22
<212> TYPE: DNA
<213> ORGANISM: Artificial Sequence
<220> FEATURE:
<223> OTHER INFORMATION: GFP_F

<400> SEQUENCE: 6
ggtgaaggtg atgctacata gg                                            22

<210> SEQ ID NO 7
<211> LENGTH: 21
<212> TYPE: DNA
<213> ORGANISM: Artificial Sequence
<220> FEATURE:
<223> OTHER INFORMATION: GFP_R

<400> SEQUENCE: 7
tcgagtttgt gtccgagaat g                                             21

<210> SEQ ID NO 8
<211> LENGTH: 21
<212> TYPE: DNA
<213> ORGANISM: Artificial Sequence
<220> FEATURE:
<223> OTHER INFORMATION: AcKRS_RT_F -continued

<400> SEQUENCE: 8
cgcggaagaa agggagaatt a                        21

<210> SEQ ID NO 9
<211> LENGTH: 19
<212> TYPE: DNA
<213> ORGANISM: Artificial Sequence
<220> FEATURE:
<223> OTHER INFORMATION: AcKRS_RT_R

<400> SEQUENCE: 9
ctttgccgtc ggactcttt                           19

<210> SEQ ID NO 10
<211> LENGTH: 22
<212> TYPE: DNA
<213> ORGANISM: Artificial Sequence
<220> FEATURE:
<223> OTHER INFORMATION: GFP_RT_F

<400> SEQUENCE: 10
ggtgaaggtg atgctacata gg                       22

<210> SEQ ID NO 11
<211> LENGTH: 21
<212> TYPE: DNA
<213> ORGANISM: Artificial Sequence
<220> FEATURE:
<223> OTHER INFORMATION: GFP_RT_R

<400> SEQUENCE: 11
tcgagtttgt gtccgagaat g                        21

<210> SEQ ID NO 12
<211> LENGTH: 22
<212> TYPE: DNA
<213> ORGANISM: Artificial Sequence
<220> FEATURE:
<223> OTHER INFORMATION: Actin_RT_F

<400> SEQUENCE: 12
gtgacgttga catccgtaaa ga                       22

<210> SEQ ID NO 13
<211> LENGTH: 19
<212> TYPE: DNA
<213> ORGANISM: Artificial Sequence
<220> FEATURE:
<223> OTHER INFORMATION: Actin_RT_R

<400> SEQUENCE: 13
gccggactca tcgtactcc                           19

<210> SEQ ID NO 14
<211> LENGTH: 4
<212> TYPE: PRT
<213> ORGANISM: Artificial Sequence
<220> FEATURE:
<223> OTHER INFORMATION: Synthetic construct

<400> SEQUENCE: 14

Met Ala Ser Lys
1

<210> SEQ ID NO 15

```
<211> LENGTH: 23
<212> TYPE: PRT
<213> ORGANISM: Artificial Sequence
<220> FEATURE:
<223> OTHER INFORMATION: Synthetic construct

<400> SEQUENCE: 15

Gly Glu Glu Leu Phe Thr Gly Val Val Pro Ile Leu Val Glu Leu Asp
1               5                   10                  15

Gly Asp Val Asn Gly His Lys
            20

<210> SEQ ID NO 16
<211> LENGTH: 15
<212> TYPE: PRT
<213> ORGANISM: Artificial Sequence
<220> FEATURE:
<223> OTHER INFORMATION: Synthetic construct

<400> SEQUENCE: 16

Phe Ser Val Ser Gly Glu Gly Glu Gly Asp Ala Thr Tyr Gly Lys
1               5                   10                  15

<210> SEQ ID NO 17
<211> LENGTH: 32
<212> TYPE: PRT
<213> ORGANISM: Artificial Sequence
<220> FEATURE:
<223> OTHER INFORMATION: Synthetic construct

<400> SEQUENCE: 17

Leu Thr Leu Lys Phe Ile Cys Thr Thr Gly Lys Leu Pro Val Pro Trp
1               5                   10                  15

Pro Thr Leu Val Thr Thr Phe Ser Tyr Gly Val Gln Cys Phe Ser Arg
            20                  25                  30

<210> SEQ ID NO 18
<211> LENGTH: 6
<212> TYPE: PRT
<213> ORGANISM: Artificial Sequence
<220> FEATURE:
<223> OTHER INFORMATION: Synthetic construct

<400> SEQUENCE: 18

Tyr Pro Asp His Met Lys
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic construct

<400> SEQUENCE: 19

Tyr Pro Asp His Met Lys Arg
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic construct

<400> SEQUENCE: 20
```

Arg His Asp Phe Phe Lys
1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic construct

<400> SEQUENCE: 21

His Asp Phe Phe Lys
1               5

<210> SEQ ID NO 22
<211> LENGTH: 11
<212> TYPE: PRT
<213> ORGANISM: Artificial Sequence
<220> FEATURE:
<223> OTHER INFORMATION: Synthetic construct

<400> SEQUENCE: 22

Ser Ala Met Pro Glu Gly Tyr Val Gln Glu Arg
1               5                   10

<210> SEQ ID NO 23
<211> LENGTH: 5
<212> TYPE: PRT
<213> ORGANISM: Artificial Sequence
<220> FEATURE:
<223> OTHER INFORMATION: Synthetic construct

<400> SEQUENCE: 23

Thr Ile Ser Phe Lys
1               5

<210> SEQ ID NO 24
<211> LENGTH: 11
<212> TYPE: PRT
<213> ORGANISM: Artificial Sequence
<220> FEATURE:
<223> OTHER INFORMATION: Synthetic construct

<400> SEQUENCE: 24

Thr Ile Ser Phe Lys Asp Asp Gly Asn Tyr Lys
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Synthetic construct

<400> SEQUENCE: 25

Thr Ile Ser Phe Lys Asp Asp Gly Asn Tyr Lys Thr Arg
1               5                   10

<210> SEQ ID NO 26
<211> LENGTH: 13
<212> TYPE: PRT
<213> ORGANISM: Artificial Sequence
<220> FEATURE:
<223> OTHER INFORMATION: Synthetic construct

<400> SEQUENCE: 26

Ala Glu Val Lys Phe Glu Gly Asp Thr Leu Val Asn Arg

<210> SEQ ID NO 27
<211> LENGTH: 17
<212> TYPE: PRT
<213> ORGANISM: Artificial Sequence
<220> FEATURE:
<223> OTHER INFORMATION: Synthetic construct

<400> SEQUENCE: 27

Ala Glu Val Lys Phe Glu Gly Asp Thr Leu Val Asn Arg Ile Glu Leu
1               5                   10                  15
Lys

<210> SEQ ID NO 28
<211> LENGTH: 9
<212> TYPE: PRT
<213> ORGANISM: Artificial Sequence
<220> FEATURE:
<223> OTHER INFORMATION: Synthetic construct

<400> SEQUENCE: 28

Phe Glu Gly Asp Thr Leu Val Asn Arg
1               5

<210> SEQ ID NO 29
<211> LENGTH: 13
<212> TYPE: PRT
<213> ORGANISM: Artificial Sequence
<220> FEATURE:
<223> OTHER INFORMATION: Synthetic construct

<400> SEQUENCE: 29

Phe Glu Gly Asp Thr Leu Val Asn Arg Ile Glu Leu Lys
1               5                   10

<210> SEQ ID NO 30
<211> LENGTH: 5
<212> TYPE: PRT
<213> ORGANISM: Artificial Sequence
<220> FEATURE:
<223> OTHER INFORMATION: Synthetic construct

<400> SEQUENCE: 30

Gly Ile Asp Phe Lys
1               5

<210> SEQ ID NO 31
<211> LENGTH: 14
<212> TYPE: PRT
<213> ORGANISM: Artificial Sequence
<220> FEATURE:
<223> OTHER INFORMATION: Synthetic construct

<400> SEQUENCE: 31

Gly Ile Asp Phe Lys Glu Asp Gly Asn Ile Leu Gly His Lys
1               5                   10

<210> SEQ ID NO 32
<211> LENGTH: 20
<212> TYPE: PRT
<213> ORGANISM: Artificial Sequence
<220> FEATURE:
<223> OTHER INFORMATION: Synthetic construct

<400> SEQUENCE: 32

```
Gly Ile Asp Phe Lys Glu Asp Gly Asn Ile Leu Gly His Lys Leu Glu
1               5                  10                 15

Tyr Asn Tyr Asn
            20

<210> SEQ ID NO 33
<211> LENGTH: 10
<212> TYPE: PRT
<213> ORGANISM: Artificial Sequence
<220> FEATURE:
<223> OTHER INFORMATION: Synthetic construct

<400> SEQUENCE: 33

Ser His Asn Val Tyr Ile Thr Ala Asp Lys
1               5                  10

<210> SEQ ID NO 34
<211> LENGTH: 32
<212> TYPE: PRT
<213> ORGANISM: Artificial Sequence
<220> FEATURE:
<223> OTHER INFORMATION: Synthetic construct

<400> SEQUENCE: 34

Gly Ile Asp Phe Lys Glu Asp Gly Asn Ile Leu Gly His Lys Leu Glu
1               5                  10                 15

Tyr Asn Tyr Asn Ser His Asn Val Tyr Ile Thr Ala Asp Lys Gln Lys
            20                  25                 30

<210> SEQ ID NO 35
<211> LENGTH: 18
<212> TYPE: PRT
<213> ORGANISM: Artificial Sequence
<220> FEATURE:
<223> OTHER INFORMATION: Synthetic construct

<400> SEQUENCE: 35

Leu Glu Tyr Asn Tyr Asn Ser His Asn Val Tyr Ile Thr Ala Asp Lys
1               5                  10                 15

Gln Lys

<210> SEQ ID NO 36
<211> LENGTH: 4
<212> TYPE: PRT
<213> ORGANISM: Artificial Sequence
<220> FEATURE:
<223> OTHER INFORMATION: Synthetic construct

<400> SEQUENCE: 36

Asn Gly Ile Lys
1

<210> SEQ ID NO 37
<211> LENGTH: 4
<212> TYPE: PRT
<213> ORGANISM: Artificial Sequence
<220> FEATURE:
<223> OTHER INFORMATION: Synthetic construct

<400> SEQUENCE: 37

Ala Asn Phe Lys
1

<210> SEQ ID NO 38
<211> LENGTH: 20
```

```
<212> TYPE: PRT
<213> ORGANISM: Artificial Sequence
<220> FEATURE:
<223> OTHER INFORMATION: Synthetic construct

<400> SEQUENCE: 38

Ile Arg His Asn Ile Glu Asp Gly Ser Val Gln Leu Ala Asp His Tyr
1               5                   10                  15

Gln Gln Asn Thr
            20

<210> SEQ ID NO 39
<211> LENGTH: 20
<212> TYPE: PRT
<213> ORGANISM: Artificial Sequence
<220> FEATURE:
<223> OTHER INFORMATION: Synthetic construct

<400> SEQUENCE: 39

Pro Ile Gly Asp Gly Pro Val Leu Leu Pro Asp Asn His Tyr Leu Ser
1               5                   10                  15

Thr Gln Ser Ala
            20

<210> SEQ ID NO 40
<211> LENGTH: 43
<212> TYPE: PRT
<213> ORGANISM: Artificial Sequence
<220> FEATURE:
<223> OTHER INFORMATION: Synthetic construct

<400> SEQUENCE: 40

Ile Arg His Asn Ile Glu Asp Gly Ser Val Gln Leu Ala Asp His Tyr
1               5                   10                  15

Gln Gln Asn Thr Pro Ile Gly Asp Gly Pro Val Leu Leu Pro Asp Asn
            20                  25                  30

His Tyr Leu Ser Thr Gln Ser Ala Leu Ser Lys
        35                  40

<210> SEQ ID NO 41
<211> LENGTH: 5
<212> TYPE: PRT
<213> ORGANISM: Artificial Sequence
<220> FEATURE:
<223> OTHER INFORMATION: Synthetic construct

<400> SEQUENCE: 41

Asp Pro Asn Glu Lys
1               5

<210> SEQ ID NO 42
<211> LENGTH: 6
<212> TYPE: PRT
<213> ORGANISM: Artificial Sequence
<220> FEATURE:
<223> OTHER INFORMATION: Synthetic construct

<400> SEQUENCE: 42

Asp Pro Asn Glu Lys Arg
1               5

<210> SEQ ID NO 43
<211> LENGTH: 20
<212> TYPE: PRT
<213> ORGANISM: Artificial Sequence
```

<220> FEATURE:
<223> OTHER INFORMATION: Synthetic construct

<400> SEQUENCE: 43

Asp His Met Val Leu Leu Glu Phe Val Thr Ala Ala Gly Ile Thr His
1               5                   10                  15

Gly Met Asp Glu
            20

<210> SEQ ID NO 44
<211> LENGTH: 31
<212> TYPE: PRT
<213> ORGANISM: Artificial Sequence
<220> FEATURE:
<223> OTHER INFORMATION: Synthetic construct

<400> SEQUENCE: 44

Asp His Met Val Leu Leu Glu Phe Val Thr Ala Ala Gly Ile Thr His
1               5                   10                  15

Gly Met Asp Glu Leu Tyr Lys Asp Tyr Lys Asp Asp Asp Lys
            20                  25                  30

<210> SEQ ID NO 45
<211> LENGTH: 5
<212> TYPE: PRT
<213> ORGANISM: Artificial Sequence
<220> FEATURE:
<223> OTHER INFORMATION: Synthetic construct

<400> SEQUENCE: 45

Asp Asp Asp Asp Lys
1               5

<210> SEQ ID NO 46
<211> LENGTH: 1516
<212> TYPE: DNA
<213> ORGANISM: Artificial Sequence
<220> FEATURE:
<223> OTHER INFORMATION: Synthetic construct

<400> SEQUENCE: 46
atgtatccat atgatgttcc agattatgct atggataaaa aaccactaaa cactctgata      60
tccgcaaccg ggctctggat gtccaggacc ggaacaattc ataaaataaa acaccacgaa     120
gtctctcgaa gcaaaatcta tattgaaatg gcatgcggag gccaccttgt tgtaaacaac    180
tccaggagca gcaggactgc aagagcgctc aggcaccaca aatacaggaa gacctgcaaa    240
cgctgcaggg tttcggatga ggatctcaat aagttcctca caaaggcaaa cgaagaccag    300
acaagcgtaa aagtcaaggt cgtttctgcc cctaccagaa cgaaaaaggc aatgccaaaa    360
tccgttgcga gagccccgaa acctcttgag aatacagaag cggcacaggc tcaaccttct    420
ggatctaaat tttcacctgc gataccggtt ccaccaagag tcagtttctg tcccggcat     480 ctgtttcaac atcaatatca agcatttcta caggagcaac tgcatccgca ctggtaaaag    540
ggaatacgaa tcccattaca tccatgtctg cccctgttca ggcaagtgcc cccgcactta    600
cgaagaacca gactgacagg cttgaagtcc tgttaaaccc aaaagatgag atttccctga    660
attccggcaa gcctttcagg gagcttgagt ccgaattgct ctctcgcaga aaaaaagacc    720
tgcagcagat ctacgcgaaa gaagggagaa ttatctggg gaaactcgag cgtgaaatta    780
ccaggttctt tgtggacagg ggttttctgg aaataaaatc cccgatcctg atccctcttg    840
agtatatcga aggatgggc attgataatg ataccgaact ttcaaaacag atcttcaggg    900

```
ttgacaagaa cttctgcctg agacccatga tggctccaaa ccttctgaac tacgcgcgca      960
agcttgacag ggccctgcct gatccaaaaa ttttttgaaat aggcccatgc tacagaaaag    1020
agtccgacgg caaagaacac ctcgaagagt ttaccatgct gaacttcttc cagatgggat    1080
cgggatgcac acgggaaaat cttgaaagca taattacgga cttcctgaac cacctgggaa    1140
ttgatttcaa gatcgtaggc gattcctgca tggtctatgg ggatacccctt gatgtaatgc    1200 acggagacct ggaactttcc tctgcagtag tcggacccat accgcttgac cgggaatggg    1260
gtattgataa accctggata ggggcaggtt tcgggctcga acgccttcta aaggttaaac    1320
acgactttaa aaatatcaag agagctgcaa ggtccgagtc ttactataac gggatttcta    1380
ccaacctgtg agcggccgct cgagcatgca tctagagggc cctattctat agtgtcacct    1440
aaatgctaga gctcgctgat cagcctcgac tgtgccttct agttgccagc catctgttgt    1500
ttgcccctcc cccgtg                                                    1516
```

<210> SEQ ID NO 47
<211> LENGTH: 1653
<212> TYPE: DNA
<213> ORGANISM: Artificial Sequence
<220> FEATURE:
<223> OTHER INFORMATION: Synthetic construct

<400> SEQUENCE: 47

```
gatctgtccc gttgattttg gtgccaaaac aaactcccat tgacgtcaat ggggtggaga      60
cttggaaatc ccggtgagtc aaaccgctat ccacgcccat tgatgtactg ccaaaaccgc    120
atcaccatgg taatagcgat gactaatacg tagatgtact gccaagtgga aagtcccata    180
aggtcatgta ctgggcataa tgccaggcgg gccatttacc gtcattgacg tcaatagggg    240
gcgtacttgg catatgatac acttgatgta ctgccaagtg gcagtttac cgtaaatact    300 ccacccattg acgtcaatgg aaagtcccta ttggcgttac tatgggaaca tacgtcatta    360
ttgacgtcaa tgggcggggg tcgttgggcg gtcagccagg cgggccattt accgtaagtt    420
atgtaacgcg gaactccata tatgggctat gaactaatga ccccgtaatt gattactatt    480
aataactagg atccaagcta caacaaggca aggcttgacc gagaattccg tgaggctccg    540
gtgcccgtca gtgggcagag cgcacatcgc ccacagtccc cgagaagttg ggggagggg    600 tcggcaattg aaccggtgcc tagagaaggt ggcgcgggt aaactgggaa agtgatgtcg    660
tgtactggct ccgccttttt cccgagggtg ggggagaacc gtatataagt gcagtagtcg    720
ccgtgaacgt tctttttcgc aacgggtttg ccgccagaac acaggtaagt gccgtgtgtg    780
gttcccgcgg gcctggcctc tttacgggtt atggcccttg cgtgccttga attacttcca    840
cctggctcca gtacgtgatt cttgatcccg agctggagcc aggggcgggc cttgcgcttt    900
aggagcccct tcgcctcgtg cttgagttga ggcctggcct gggcgctggg ccgccgcgt    960 gcgaatctgg tggcaccttc gcgcctgtct cgctgctttc gataagtctc tagccattta   1020 aaattttga tgacctgcga cgcttttttt ctggcaagat agtcttgtaa atgcgggcca    1080
ggatctgcac actggtattt cggttttttgg ggccgcgggc ggcgacgggg cccgtgcgtc   1140
ccagcgcaca tgttcggcga ggcggggcct gcgagcgcgg ccaccgagaa tcggacgggg   1200
gtagtctcaa gctggccggc ctgctctggt gcctggcctc gcgccgccgt gtatcgcccc   1260
gccctgggcg gcaaggctgg cccggtcggc accagttgcg tgagcggaaa gatgccgcgt   1320
tcccggccct gctccagggg gctcaaaatg gaggacgcgg cgctcgggag agcgggcggg   1380
```

```
tgagtcaccc acacaaagga aagggg cctt tccgtcctca gccgtcgctt catgtgactc    1440
cacggagtac cgggcgccgt ccaggcacct cgattagttc tggagctttt ggagtacgtc    1500
gtcgtttagg ttgggggag gggttttatg cgatggagtt tccccacact gagtgggtgg    1560
agactgaagt taggccagct tggcacttga tgtaattctc cttggaattt gcccttttg    1620 agtttggatc ttggttcatt ctcaagcctc aga                                  1653
```

TRANSGENIC MOUSE CAPABLE OF SPATIAL AND TEMPORAL CONTROL OF EXPRESSION AND SITE-SPECIFIC MODIFICATION OF TARGET PROTEIN, PRODUCTION METHOD AND USES THEREOF

CROSS-REFERENCE TO RELATED APPLICATION

This application claims the benefit under 35 USC § 119 of U.S. Provisional Patent Application No. 62/383,560 filed Sep. 5, 2016. The disclosure of such application is hereby incorporated herein by reference in its entirety, for all purposes.

REFERENCE TO SEQUENCE LISTING SUBMITTED VIA EFS-WEB

This application includes an electronically submitted sequence listing in .txt format. The .txt file contains a sequence listing entitled "337UpdatedSequenceListing_ST25.txt" created on Aug. 2, 2020 and is 29,231 bytes in size. The sequence listing contained in this .txt file is part of the specification and is hereby incorporated by reference herein in its entirety.

TECHNICAL FIELD

The present invention relates to a mouse (Mus musculus) in which expression and site-specific modification of a target protein is temporally and spatially controlled, and a method for producing the same and the uses thereof, and more particularly to a transgenic mouse in which expression and site-specific modification of a target protein is temporally and spatially controlled as a result of incorporation of an unnatural amino acid.

BACKGROUND ART

Post-translational modifications (PTMs) play a crucial role in expanding the diversity of protein function and also have various important effects on in vivo activity (Walsh et al., Angew. Chem. Vol. 44, pp. 3742-7372. 2005). The amber codon suppression technique, based on the use of an orthogonal aminoacyl-tRNA synthetase/tRNA pair, has been successfully developed as a means to expand a protein's functionalities in a laboratory (Liu et al., Annu. Rev. Biochem. Vol. 79, pp. 413-444. 2010). This approach has been widely used to examine various aspects of proteins at the molecular and cellular level. Up to now, this technique has been applied to expand the genetic code of bacteria, yeast, mammals, stem cells, neurons, primitive animals, insects and plants.

However, despite extensive efforts, this powerful approach has not been extended to the multiorgan animal mouse (Mus musculus), the most prevalent model of human physiology and disease. The mouse is known to be a model organism whose genome is most closely related to that of humans: its genome is more than 99% similar to that of humans, and it contains most human gene counterparts or functionally related genes (Rosenthal et al., Nat. Cell. Biol. Vol. 9, pp. 993-999. 2007). The mouse has short life span and is easy to breed and handle in a laboratory. More importantly, the mouse genome is readily manipulated, which makes it possible to generate custom-made mutant mouse strains, enabling detailed in vivo study of specific genes and providing excellent models for various human diseases (Schvartzman et al., Nat. Rev. Cancer. Vol 10. pp. 102-115. 2010).

Meanwhile, lysine acetylation is a reversible post-translational modification that dynamically regulates functions of a wide range of eukaryotic proteins; thus, it critically affects numerous cellular processes (Choudhary et al., Nat. Rev. Mol. Cell. Biol. Vol. 15, pp. 536-550. 2014). In particular, aberrant acetylation of many cellular proteins is associated with various human diseases, including cancer.

However, detailed functional analyses of protein acetylation have been hampered by technical difficulties in controlling acetylation in animal cells. Recently, the present inventors and other research teams have developed techniques enabling selective chemical modifications in proteins, including phosphorylation and acetylation (Yang et al., Science. Vol 354. pp. 623-626. 2016).

Under this background, the present inventors have made extensive efforts to produce a mouse in which site-specific modification of a target protein can be temporally and spatially controlled. As a result, the present inventors have found that when a mouse is constructed by introducing a tRNA synthetase specific for an unnatural amino acid, a tRNA that recognizes the unnatural amino acid, and a gene that encodes a target protein carrying an amber codon, a mouse in which site-specific modification of a target protein is controlled depending on the timing and/or position of the unnatural amino acid that is introduced can be produced, thereby completing the present invention.

The information disclosed in the Background Art section is only for the enhancement of understanding of the background of the present invention, and therefore may not contain information that forms a prior art that would already be known to a person of ordinary skill in the art.

DISCLOSURE OF INVENTION

Technical Problem

It is an object of the present invention to provide a mouse in which site-specific modification of a target protein is temporally and spatially controlled.

Another objet of the present invention is to provide a method for producing a mouse in which site-specific modification of a target protein is temporally and spatially controlled.

Still another objet of the present invention is to provide the use of a mouse in which site-specific modification of a target protein is temporally and spatially controlled.

Yet another objet of the present invention is to provide a method for regulating expression of a target protein in a mouse in which site-specific modification of the target protein is temporally and spatially controlled.

Technical Solution

To achieve the above objects, the present invention provides a tRNA synthetase expression vector comprising: a human elongation factor 1-α promoter; a gene encoding $N^\varepsilon$-acetyl-lysyl-tRNA synthetase (AcKRS); a CMV immediately early enhancer; an RNA polymerase III promoter U6; and a gene encoding tRNA$^{pyl}$.

The present invention also provides a target protein expression vector carrying an amber codon at a specific position, the expression vector comprising: a human elongation factor 1-α promoter; a gene encoding a target protein carrying the amber codon at a specific position; a CMV immediately early enhancer; an RNA polymerase III promoter U6; and a gene encoding tRNA$^{pyl}$.

The present invention also provides a mouse having an AcKRS/+;tRNA$^{pyl}$/+, target protein-amber/+;tRNA$^{pyl}$/+ genotype as a result of introduction of the above-described tRNA synthetase expression vector and the above-described target protein expression vector carrying an amber codon at a specific position.

The present invention also provides a method for producing a mouse having an AcKRS/+;tRNA$^{pyl}$/+, target protein-amber/+;tRNA$^{pyl}$/+ genotype, the method comprising the steps of:

(a) linearizing the above-described tRNA synthetase expression vector, microinjecting the linearized expression vector into fertilized mouse eggs, transferring the fertilized eggs into a surrogate, and then allowing the surrogate to give birth, thereby producing a first mouse having an AcKRS/+; tRNA$^{pyl}$/+ genotype;

(b) linearizing the above-described target protein expression vector carrying an amber codon at a specific position, microinjecting the linearized expression vector into fertilized mouse eggs, transferring the fertilized eggs into a surrogate, and then allowing the surrogate to give birth, thereby producing a second mouse having a target protein-amber/+;tRNA$^{pyl}$/+ genotype; and (c) crossing the first mouse with the second mouse, thereby producing a mouse having an AcKRS/+;tRNA$^{pyl}$/+, target protein-amber/+;tRNA$^{pyl}$/+ genotype.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 5A shows the results of sequencing of AcKRS (AcKRS cDNA, SEQ ID NO: 46), and FIG. 5B shows the results of sequencing of GFPamber (GFPamber cDNA, SEQ ID NO: 47).

BEST MODE FOR CARRYING OUT THE INVENTION

Figure 1A:
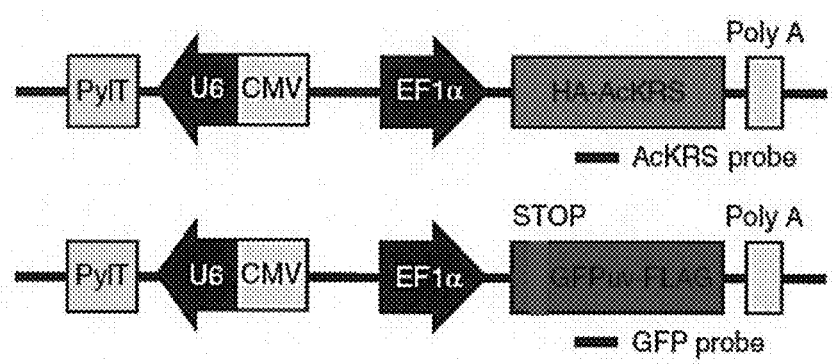
FIG. 1A is a schematic diagram showing a vector (Pyl:: HA-AcKRS, PylT::GFP39TAG-FLAG® protein) used to construct a mouse according to an example of the present invention, and the positions of probes used to examine the position of an inserted gene.

Unless defined otherwise, all technical and scientific terms used herein have the same meaning as commonly understood by one of ordinary skill in the art to which the invention pertains. Generally, the nomenclature used herein and the experiment methods, which will be described below, are those well known and commonly employed in the art.

As used herein, the term "protein modification" means that a specific compound binds to the residue portion of an amino acid synthesized after protein synthesis (a step in which mRNA transcribed from DNA is translated into an amino acid primary chain). The term may be "post-translational modification (PTM)", but is not limited thereto.

In the present invention, the protein modification moiety can be used without any limitation as long as it is a PTM moiety of a protein that is generally well-known, and may be preferably produced by at least one reaction selected from the group consisting of acylation, alkylation, amidation, butyrylation, carboxylation, glycosylation, formylation, hydroxylation, iodination, oxidation, phosphorylation, propionylation, succinylation, sulfation, glycation, carbonylation, formylation, ubiquitination, sumoylation, neddylation, and pupylation, but is not limited thereto.

In the present invention, the alkylation can be used without any limitation as long as it is a chemical reaction that produces an atomic group by removing one hydrogen atom from an aliphatic saturated hydrocarbon. The alkylation may be preferably selected from the group consisting of mono-methylation), di-methylation, tri-methylation, acetylation, ethylation, propylation, amylation, hexylation, heptylation, octylation, nonylation, and decylation. Most preferably the alkylation may be acetylation, but is not limited thereto.

In the present invention, an attempt has been made to confirm whether site-specific modification of a target protein in mice would be temporally and spatially controlled using an orthogonal tRNA synthetase/unnatural tRNA pair.

Specifically, in one example of the present invention, a tRNA synthetase expression vector comprising: a human elongation factor 1-α promoter; a gene encoding $N^\varepsilon$-acetyl-lysyl-tRNA synthetase (AcKRS); a CMV immediately early enhancer; an RNA polymerase III promoter U6; and a gene encoding tRNA$^{pyl}$; and a GFPuv39TAG expression vector comprising: a human elongation factor 1-α promoter; a gene encoding a GFPuv protein carrying the amber codon at a position 39; a CMV immediately early enhancer; an RNA polymerase III promoter U6; and a gene encoding tRNA$^{pyl}$ were constructed (FIGS. 1A-1E) and introduced into different mice. The mice were mated with each other to generate mice having an AcKRS/+, GFPamber/+ genotype. Then, it could be seen that expression of GFP in the mice could be controlled depending on the position and/or timing of incorporation of an unnatural amino acid (AcK, tfAcK or BrF) (FIGS. 8A-8C, FIG. 9, and FIG. 11A-11B).

Therefore, in one aspect, the present invention is directed to a tRNA synthetase expression vector comprising: a human elongation factor 1-α promoter; a gene encoding $N^\varepsilon$-acetyl-lysyl-tRNA synthetase (AcKRS); a CMV immediately early enhancer; an RNA polymerase III promoter U6; and a gene encoding tRNA$^{pyl}$.

Also, in another aspect, the present invention is directed to a target protein expression vector carrying an amber codon at a specific position, the expression vector comprising: a human elongation factor 1-α promoter; a gene encoding a target protein carrying the amber codon at a specific position; a CMV immediately early enhancer; an RNA polymerase III promoter U6; and a gene encoding tRNA$^{pyl}$.

In the present invention, the gene encoding $N^\varepsilon$-acetyl-lysyl-tRNA synthetase (AcKRS) may comprise a nucleotide sequence represented by SEQ ID NO: 1, but is not limited thereto.

In the present invention, the gene encoding tRNA$^{pyl}$ may comprise a nucleotide sequence represented by SEQ ID NO: 2, but is not limited thereto.

In the present invention, the tRNA synthetase expression vector may comprise a nucleotide sequence represented by SEQ ID NO: 3, but is not limited thereto.

The target protein that is used in the present invention can be used without any limitation as long as it is a protein whose coding sequence is known for function studies. The target protein may be preferably a protein in which modification including acetylation can be attached to a specific position. More preferably, the target protein may be selected from the group consisting of histone protein, tau protein, p53, β-catenin, NF-κB, MyoD, Rb, tubulin, STAT3, Elp3, North, TGF-β, p300, MYST protein, AceCS1, LCAD, EHHADH, MDH, SDH, ASL, CPS1, OTC, PDHA1, aconitase, FOXO1, SAGA complex, Myc, SIRT protein, N—CoR1/2, PPARα/β/γ, LXR, mTOR, MEF2, PEPCK-C, and G6pase, but is not limited thereto.

In still another aspect, the present invention is directed to a mouse (*Mus musclus*) having an AcKRS/+;tRNA$^{pyl}$/+, target protein-amber/+;tRNA$^{pyl}$/+ genotype as a result of introduction of a tRNA synthetase expression vector comprising: a human elongation factor 1-α promoter; a gene encoding $N^\varepsilon$-acetyl-lysyl-tRNA synthetase (AcKRS); a CMV immediately early enhancer; an RNA polymerase III promoter U6; and a gene encoding tRNA$^{pyl}$, and a target protein expression vector carrying an amber codon at a specific position, the expression vector comprising: a human elongation factor 1-α promoter; a gene encoding a target protein carrying the amber codon at a specific position; a CMV immediately early enhancer; an RNA polymerase III promoter U6; and a gene encoding tRNA$^{pyl}$.

In the present invention, the target protein may be a protein incorporated with an unnatural amino acid at a specific position.

In the present invention, the unnatural amino acid can be used without any limitation as long as it is an amino acid that can be detected by a tRNA that recognizes the unnatural amino acid. Preferably, the unnatural amino acid may be selected from the group consisting of $N^\varepsilon$-acetyl-lysine, $N^\varepsilon$ trifluoroacetyl-lysine, and 3-bromo-phenylalanine, but is not limited thereto.

In the present invention, expression of the target protein may be regulated depending on the timing or position of incorporation of an unnatural amino acid.

In the present invention, the expression and site-specific modification of a target protein is spatially controlled by directly introducing the unnatural amino acid selectively to the desired position or tissue.

In the present invention, when the timing of the unnatural amino acid is controlled by feed, the target protein may be expressed 1 to 5 days after feeding, but is not limited thereto.

In the present invention, when the position of incorporation of an unnatural amino acid is regulated by incorporating the unnatural amino acid at a specific position using a syringe, the target protein may be expressed only at the corresponding position.

In the present invention, the specific position can be used without any limitation as long as it is an in vivo site in the mouse, which can be distinguished from other sites. Preferably, the specific position may be selected from the group consisting of skin, brain, muscle, intestine, liver, kidney, lung, stomach, and heart, but is not limited thereto.

In yet another aspect, the present invention is directed to a method for producing a mouse having an AcKRS/+; tRNA$^{pyl}$/+, target protein-amber/+;tRNA$^{pyl}$/+ genotype, the method comprising the steps of: (a) linearizing a tRNA synthetase expression vector comprising: a human elongation factor 1-α promoter; a gene encoding N$^ε$-acetyl-lysyl-tRNA synthetase (AcKRS); a CMV immediately early enhancer; an RNA polymerase III promoter U6; and a gene encoding tRNA$^{pyl}$, microinjecting the linearized expression vector into fertilized mouse eggs, transferring the fertilized eggs into a surrogate, and then allowing the surrogate to give birth, thereby producing a first mouse having an AcKRS/+; tRNA$^{pyl}$/+ genotype; (b) linearizing a target protein expression vector carrying an amber codon at a specific position, the expression vector comprising: a human elongation factor 1-α promoter; a gene encoding a target protein carrying the amber codon at a specific position; a CMV immediately early enhancer; an RNA polymerase III promoter U6; and a gene encoding tRNA$^{pyl}$, microinjecting the linearized target protein expression vector into fertilized mouse eggs, transferring the fertilized eggs into a surrogate, and then allowing the surrogate to give birth, thereby producing a second mouse having a target protein-amber/+;tRNA$^{pyl}$/+ genotype; and (c) crossing the first mouse with the second mouse, thereby producing a mouse having an AcKRS/+;tRNA$^{pyl}$/+, target protein-amber/+;tRNA$^{pyl}$/+ genotype.

The present invention is also directed to the use of a mouse in which site-specific modification of a target protein is temporally and spatially controlled. In the mouse developed in the present invention, the target protein-encoding gene carries an amber codon at a specific position, and thus is not normally expressed, and translation of the gene is abnormally completed. However, the mouse has a tRNA that corresponds to the amber codon and that can recognize an unnatural amino acid, and thus when the corresponding unnatural amino acid is incorporated into the mouse in a temporally and spatially different manner, the target protein is expressed only at the position or timing of incorporation of the unnatural amino acid. Due to this characteristic, the mouse is the world's first model mouse that enables studies on the function of post-translational modification of the target protein to be performed in vivo.

Figure 11A:
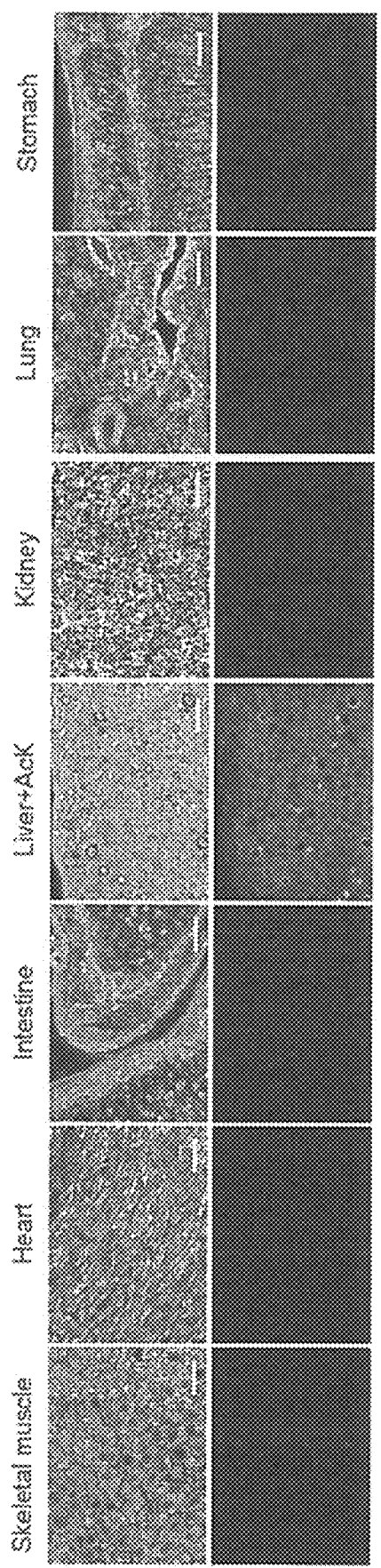
FIGS. 11A-11B show the results of examining tissue specific expression of acetylated GFPuv, and indicate that acetylated GFPuv was observed in liver (FIG. 11A) or kidney (FIG. 11B) only when AcK was injected into the corresponding tissues.
Figure 11B:
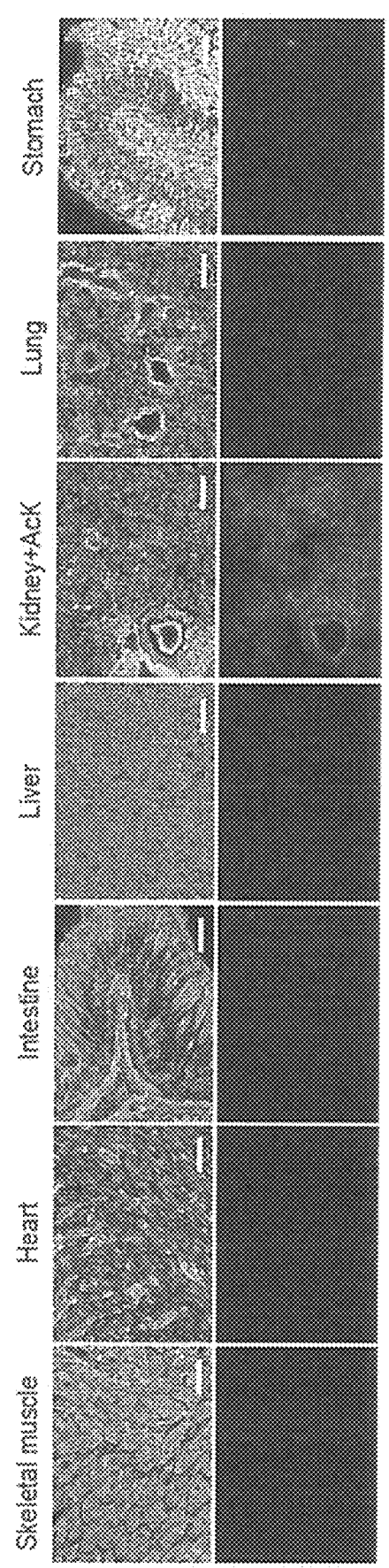

The present invention is also directed to a method for regulating expression of a target protein in a mouse in which site-specific modification of the target protein is temporally and spatially controlled. In the present invention, when the timing and position of incorporation of an unnatural amino acid are selected, expression and site-specific modification of the target protein can be temporally and spatially controlled. For example, if the mouse is fed with an unnatural amino acid, expression of the target protein in various organs (muscle, liver, lung, heart, intestine, kidney and stomach) can be detected 1 to 5 days after feeding (FIG. 9), and if an unnatural amino acid is introduced into a specific position or tissue (e.g., liver or kidney), expression of the target protein can be detected only in the corresponding site (FIGS. 11A-11B).

EXAMPLES

Hereinafter, the present invention will be described in further detail with reference to examples. It will be obvious to a person having ordinary skill in the art that these examples are for illustrative purposes only and are not to be construed to limit the scope of the present invention.

Experimental Methods

Experimental methods used in examples of the present invention are as follows.

Construction of Plasmids

An N$^ε$-acetyl-lysyl-tRNA synthetase/tRNA$^{pyl}$ pair developed from bacteria was used (Umehera et al., FEBS Lett. Vol. 586, pp. 729-733. 2012). For ubiquitous expression of AcKRS, the CMV promoter in pCDNA3 was replaced with a human elongation factor 1α promoter. Then, the gene encoding N-terminally HA-tagged AcKRS was cloned between KpnI and NotI restriction enzymes, thereby generating a plasmid pAcKRS.

To construct a tRNA$^{pyl}$ expression cassette, the gene coding for tRNA$^{pyl}$ and the RNA polymerase III promoter U6 was synthesized (Bioneer, Korea), and the CMV immediately early region enhancer was cloned from a pCDNA5 frt/TO vector (Invitrogen, USA). The expression cassette was cloned into the pAcKRS plasmid using BamHI and AscI restriction enzymes, thereby constructing a pAcKRS-tRNA plasmid.

For expression of GFPuv that is a kind of target protein, a C-terminally FLAG® protein-tagged GFPuv gene carrying an amber stop codon at position 39 was cloned in place of the AcKRS gene in the plasmid, thereby constructing pGFPamber-tRNA.

Site-Specific Incorporation of Unnatural Amino Acids (UAAs) in Mammalian Cells

Human embryonic kidney (HEK) 293 cells (HEK293) (Sigma-Aldrich) were grown in Dulbecco's modified Eagle's medium (DMEM) containing 10% fetal bovine serum (FBS) at 37° C. with 5% $CO_2$. The cells were co-transfected with 25 μg of pAckRS-tRNA and pGFPamber-tRNA plasmids using LIPOFECTAMINE® 2000 transfection reagent (Invitrogen, USA) in 100-mm dishes. After 8 hours of incubation, the medium was replaced with fresh DMEM containing 10% FBS and 10 mM UAA (N$^ε$-acetyl-lysine(AcK), N$^ε$-trifluoroacetyl-lysine (tfAcK) or 3-bromophenylalanine (BrF). The cells were collected after 40 hours of incubation.

NIH3T3 cells (ATCC) were seeded into 100-mm dish and grown in DMEM containing 10% FBS for 24 hour. At about 50% confluence, the cells were transfected with 40 μg of plasmids pAckRS-tRNA and pGFPamber-tRNA plasmids using LIPOFECTAMINE® 2000 transfection reagent (Invitrogen, USA). After overnight incubation, the medium was replaced with fresh DMEM containing 10% FBS and 10 mM UAA. The cells were collected 48 hours of incubation.

Construction of Transgenic Mice

The present inventors created an AcKRS mouse which expresses AcKRS and tRNA$^{pyl}$, and a GFPamber mouse which expresses GFPuv with amber stop codon at position 39 and tRNA$^{pyl}$.

To this end, pAcKRS-tRNA and pGFPamber-tRNA plasmids were linearized with ApaLI and PvuII restriction enzymes, and then microinjected into the fertilized mouse eggs of a C57BL/6J mouse strain (Gordon et al., Science. Vol. 214. pp. 1244-1246. 1981). PCR was performed using the primers shown in Table 1 below in order to confirm whether each gene would be correctly inserted in the AcK mouse and the GFPamber mouse.

TABLE 1

Sequences of detection primers

| Name | SEQ ID NO: | Sequence |
| --- | --- | --- |
| AcKRS_F | 4 | 5'-CGAAGACCAGACAAGCGTAAA-3' |
| AcKRS_R | 5 | 5'-CTTGAGTCCGAATTGCTCTCTC-3' |
| GFP_F | 6 | 5'-GGTGAAGGTGATGCTACATAGG-3' |
| GFP_R | 7 | 5'-TCGAGTTTGTGTCCGAGAATG-3' |

Next, to generate a double heterozygote transgenic mouse (AcK-GFPamber mouse), the AcK mouse (AcKRS/+) was mated to the GFPamber mouse (GFPamber/+). The genotype of the double-transgenic mouse was determined by PCR analysis and Southern blot analysis. To perform Southern blot analysis, the genomic DNA of the double-transgenic mouse was isolated by the phenol/chloroform extraction method, and then digested with BamHI and SphI restriction enzymes, and electrophoresed on an agarose gel. Chromosome-integrated AcKRS and GFPamber transgenes were detected with isotope-labeled cDNA probes after transfer to a positively charged nylon membrane.

All transgenic mice were generated at the Laboratory Animal Research Center at Yonsei University. All animal experiments were performed in accordance with Korean Food and Drug Administration guidelines. Experimental protocols were approved by the Institutional Animal Care and Use Committee of Yonsei University (YLARC 2012-0087). All mice were maintained in the specific pathogen-free facility of the Yonsei Laboratory Animal Research Center.

RT-PCR Analysis of AcKRS and GFPamber Transgenes

To examine the expression of AcKRS and GFPamber transgenes in different mouse tissues, RNA was isolated from mouse brain and kidney. A 305-bp cDNA fragment was amplified from the RNA by using primers shown in Table 2 below.

TABLE 2

Sequences of RT-PCR primers

| Name | SEQ ID NO: | Sequence |
| --- | --- | --- |
| AcKRS_RT_F | 8 | 5'-CGCGGAAGAAAGGGAGAATTA-3' |
| AcKRS_RT_R | 9 | 5'-CTTTGCCGTCGGACTCTTT-3' |
| GFP_RT_F | 10 | 5'-GGTGAAGGTGATGCTACATAGG-3' |
| GFP_RT_R | 11 | 5'-TCGAGTTTGTGTCCGAGAATG-3' |
| Actin_RT_F | 12 | 5'-GTGACGTTGACATCCGTAAAGA-3' |
| Actin_RT_R | 13 | 5'-GCCGGACTCATCGTACTCC-3' |

The expression levels were measured using expression of actin as a control.

Treatment of Transgenic Mouse

Animals were housed under a 12-hr light/dark cycle in standard animal cages and were provided with food and water ad libitum. To induce expression of acetylated GFP, 50 mg of AcK (Sigma) dissolved in PBS was intraperitoneally injected into 8-week-old double-transgenic mice (AcKRS/+, GFPamber/+) on a daily basis. For a control experiment, two 8-week-old double-transgenic mice were injected with PBS in the same manner. After 5 days of AcK injection, the double-transgenic mice were killed, and desired tissues were collected. For tissue-specific induction of acetylated GFP expression, 50 mg of AcK was injected directly into target tissues. In the present invention, a mixture of male and female animals was used.

Fluorescence Microscopic Analysis of Mouse Tissues

Immediately after killing, tissues were collected from double-transgenic mouse (AcKRS/+, GFPamber/+), and then embedded in TISSUE-TEK® O.C.T. compound (Sakura Finetek) and stored at −80° C. Following cryo-sectioning of the tissue blocks, frozen sections with a thickness of 20 mm were prepared, and mounted on glass slides. Then, GFPuv fluorescence was detected using a fluorescence microscope (AXIOVERT® 200FI fluorescence microscope, Zeiss), and the images were captured and digitalized using the AXIOVISION® software (Zeiss).

Mouse Embryonic Fibroblasts

Primary MEF cells were established from double-transgenic mouse embryos at 13.5 dpc (Terzioglu et al., Cell Metab. Vol. 17, pp. 618-626. 2013). Briefly, whole embryos were collected from pregnant mice and minced. The embryos were then incubated with 0.05% trypsin at 37° C. for 15 minutes and plated in DMEM (Life Technologies) containing 10% FBS (Sigma). The genotype of the embryos was identified with DNA isolated from established MEF cells. For induction of acetylated GFP expression, 10 mM AcK was added to culture medium. The expression of acetylated GFP was visualized by fluorescence microscopy after 24 hours of culture.

Down-Regulation of Mouse Upf2 Expression Using siRNA

For knockdown of Upf2 in MEF cells. MEF cells ($2\times10^6$) were grown in DMEM media containing 10% FBS, and then transiently transfected with 100 nM of siRNA (SEQ ID NO: 14: 5'-UUUAGGUUGAUUAACCUCCAUUCCC-3') specific for Upf2. siRNA specific for mouse Upf2 and control siRNA were purchased from Bioneer.

Lentivirus-Mediated Downregulation of Mouse Upf2

Mouse shRNA (SEQ ID NO: 15: 5'-TTTAGGTTGAT-TAACCTCCATTCCC-3') against mouse Upf2 was cloned into the lentiviral vector pLKO.1-TRC (Addgene), thereby constructing a pLKO.1-Upf2 plasmid. To produce lentiviral particles, the plasmid was transfected into 293TN cells (System Biosciences) together with pGag-pol and pVSV-G plasmids. 48 Hours after transfection, viral particles were collected and infected into MEF cells. The infected MEF cells were selected by 1 µg/ml of puromycin for one week.

Immunoprecipitation and Western Blot Analysis

To extract proteins, about 100 mg of cells and tissue samples were homogenized in a lysis buffer (50 mM Tris-HCl, pH7.4, 150 mM NaCl, 2 mM EDTA, 1% (v/v) TRITON' X-100 non-ionic detergent, 0.1% NP$^{40}$™ detergent, protease inhibitor cocktail) using a bead homogenizer (MP Biomedicals). After sonication using a BIORUPTOR® UCD-200 sonicator (Diagenode), the resulting lysates were centrifuged at 12,000×g for 5 minutes at 4° C., and the supernatant was collected.

The supernatant was mixed with 20 μg of anti-FLAG® protein magnetic beads (Sigma), and then incubated for 12 hours at 4° C. After washing the beads twice with cold washing buffer (50 mM Tris-HCl, 150 mM NaCL, pH 7.4), and GFP was eluted using elution buffer (0.1M Glycine-HCl, pH 3.0). The eluates were immediately neutralized using 1.0M Tris-HCl (pH 8.0). Next, Western blot analysis was performed according to a standard procedure using anti-GFP (Abcam, Cat. No. ab6556 at 1:1,000 dilution), anti-FLAG® protein (Abcam, Cat. No. ab1257 at 1:1,000 dilution) and anti-acetyl-lysine (BioLegend, Cat. No. 623402, at 1:200 dilution) antibodies.

Mass Analysis Protein samples were electrophoresed on 15% SDS-PAGE gel, and the protein band was excised from the gel, followed by in-gel tryptic digestion. Briefly, the excised band was cut into small pieces and de-stained by treatment with 100 mM ammonium bicarbonate/acetonitrile (1:1, v/v) for 30 minutes. Then, the gel pieces were mixed with 500 ml of neat acetonitrile and incubated at room temperature. After removing the acetonitrile solution, the gel pieces were treated with a solution of 10 ng/ml of trypsin (10 mM ammonium bicarbonate, 10% acetonitrile (v/v)) and incubated on ice for 2 hours, and then incubated overnight in an incubator at 37° C. 0.5 μl of the trypsin-digested sample was mixed with 1.5 μd of a matrix solution (20 mg/ml 2,5-dihydoxybenzoic acid(DHB) dissolved in 0.1% TFA in acetonitrile/water, 1:1). 1 μl of the mixture was spotted on a ground steel MTP384 for analysis. The mass data were acquired on a Bruker AUTOFLEX® III MALDI-TOF mass spectrometer.

Example 1: Construction of AcK-Incorporated System

The present inventors constructed a tRNA$^{pyl}$-containing pAcKRS-tRNA plasmid in which the expression of HA-tagged AcKRS is controlled by the EF1α promoter and the transcription of tRNA$^{pyl}$ is driven by the RNA polymerase III promoter U6 and the CMV immediately early region enhancer, and a pAcKRS-tRNA plasmid in which the gene encoding a C-terminally FLAG® protein-tagged GFPuv gene carrying an amber stop codon at position 39 was cloned in place of the AcKRS gene in the pAcKRS-tRNA plasmid (FIG. 1A).

Example 2: Validation of AcK Incorporation in Mammalian Cells

Figure 1B:
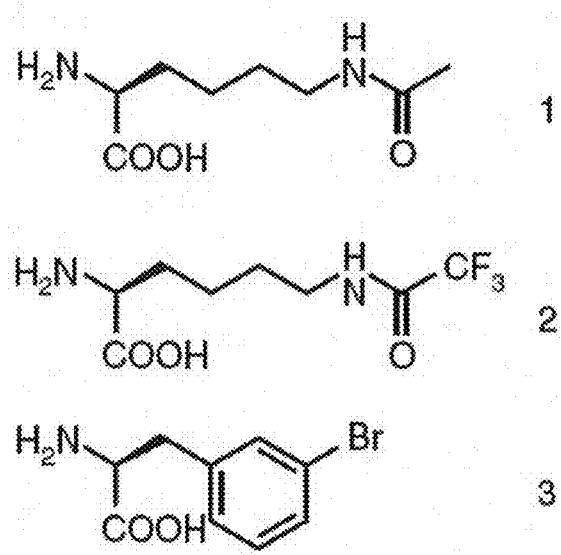
FIG. 1B shows unnatural amino acids (N$^ε$-acetyl-lysine, 1, (AcK), N$^ε$-trifluoroacetyl-lysine, 2, (tfAcK) and 3-bromo-phenylalanine, 3, BrF)) used in an example of the present invention.
Figure 1C:
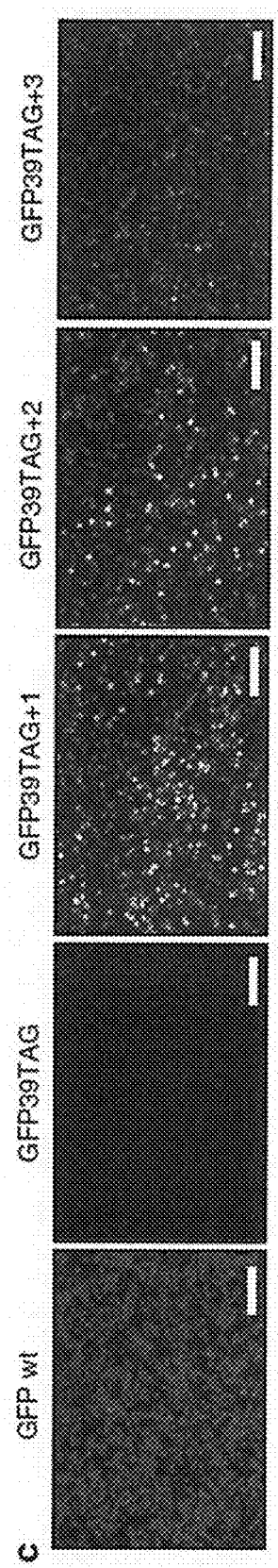
FIG. 1C shows a fluorescence image of HEK293T cells transfected with the vector of the present invention and cultured in the presence of an unnatural amino acid, AcK, tfAcK or BrF.
Figure 1D:
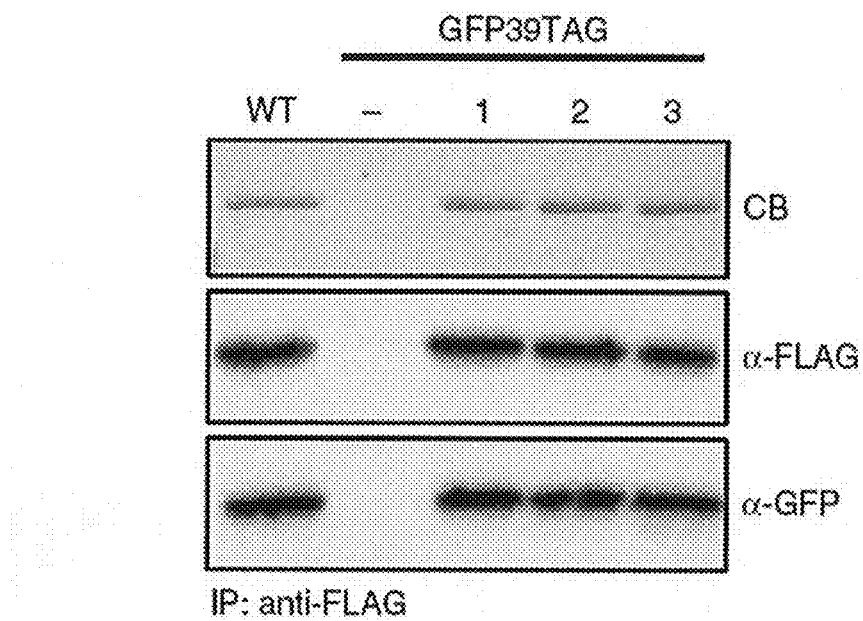
FIG. 1D shows the results of Western blot analysis of anti-FLAG® protein—immunoprecipitated proteins from lysates of cells transfected with the vector of the present invention, performed anti-FLAG® protein-tag antibody and anti-GFPuv antibody.
Figure 1E:
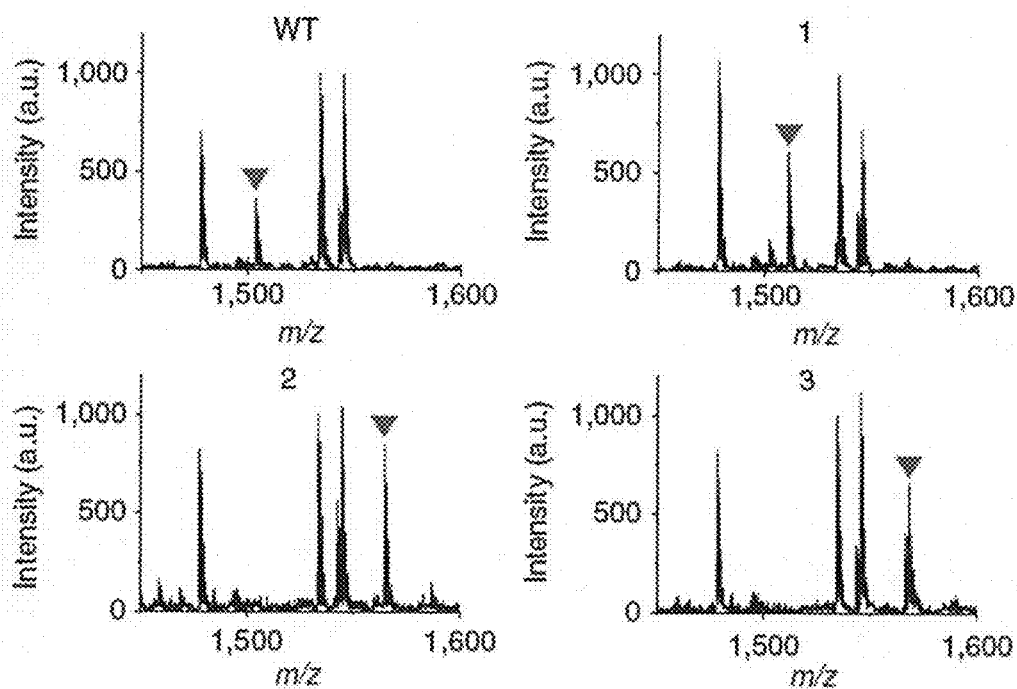
FIG. 1E the results of MALDI-TOF MS analysis of target proteins incorporated with unnatural amino proteins, performed after trypsin digestion.
Figure 2:
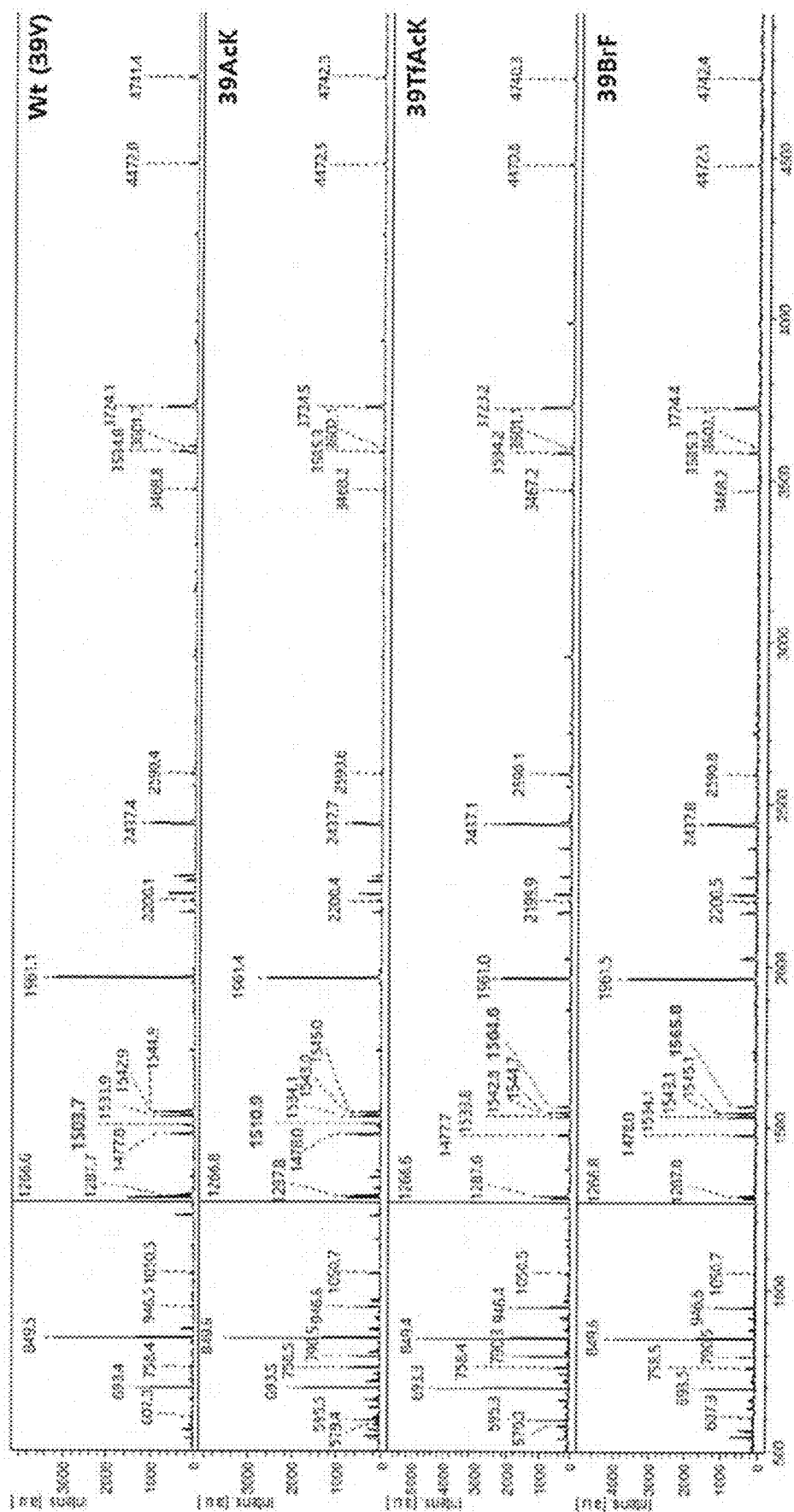
FIG. 2 shows the mass spectrum of in-gel trypsin digestion of GFPuv wild-type protein and mutant proteins carrying unnatural amino acids at position 39 (39AcK, 39TfAcK, and 39BrF). Each peak in the spectrum (top) represents a tryptic peptide (bottom). The peptide sequences in the table below the mass spectrum include: MASK (SEQ ID NO: 14); GEELFTGVVPILVELDGDVNGHK (SEQ ID NO: 15); FSVSGEGEGDATYGK (SEQ ID NO: 16); LTLKFICTTGKLPVPWPTLVTTFSYGVQCFSR (SEQ ID NO: 17); YPDHMK (SEQ ID NO: 18); YPDHMKR (SEQ ID NO: 19); RHDFFK (SEQ ID NO: 20); HDFFK (SEQ ID NO: 21); SAMPEGYVQER (SEQ ID NO: 22); TISFK (SEQ ID NO: 23); TISFKDDGNYK (SEQ ID NO: 24); TISFKDDGNYKTR (SEQ ID NO: 25); AEVKFEGDTLVNR (SEQ ID NO: 26); AEVKFEGDTLVNRIELK (SEQ ID NO: 27); FEGDTLVNR (SEQ ID NO: 28); FEGDTLVNRIELK (SEQ ID NO: 29); GIDFK (SEQ ID NO: 30); GIDFKEDGNILGHK (SEQ ID NO: 31); GIDFKEDGNILGHKLEYNYN (SEQ ID NO: 32); SHNVYITADK (SEQ ID NO: 33); GIDFKEDGNILGHKLEYNYNSHNVYITADKQK (SEQ ID NO: 34); LEYNYNSHNVYITADKQK (SEQ ID NO: 35); NGIK (SEQ ID NO: 36); ANFK (SEQ ID NO: 37); IRHNIEDGSVQLADHYQQNT (SEQ ID NO: 38); PIGDGPVLLPDNHYLSTQSA (SEQ ID NO: 39); IRHNIEDGSVQLADHYQQNTPIGDGPVLLPDNHYLSTQSALSK (SEQ ID NO: 40); DPNEK (SEQ ID NO: 41); DPNEKR (SEQ ID NO: 42); DHMVLLEFVTAAGITHGMDE (SEQ ID NO: 43); DHMVLLEFVTAAGITHGMDELYKDYKDDDDK (SEQ ID NO: 44); and DDDDK (SEQ ID NO: 45).

The two plasmids constructed in Example 1 were transfected into HEK293T cells, and then treated with AcK. As a result, it could be seen that fluorescence signals were detected only in cells incubated with AcK (FIGS. 1B and 1C). Two other unnatural amino acids (tfAcK, and BrF) were also tested, and as a result, it could be seen that fluorescence was detected only in the presence of each unnatural amino acid. Furthermore, Western blotting analysis was performed using anti-FLAG® protein and anti-GFP antibodies, and as a result, it could be seen that the band appeared only in the presence of the unnatural amino acid (FIG. 1D). In addition, MALDI-TOF MS analysis indicated that the unnatural amino acid was correctly incorporated into the amber codon site (FIG. 2).

Figure 3A:
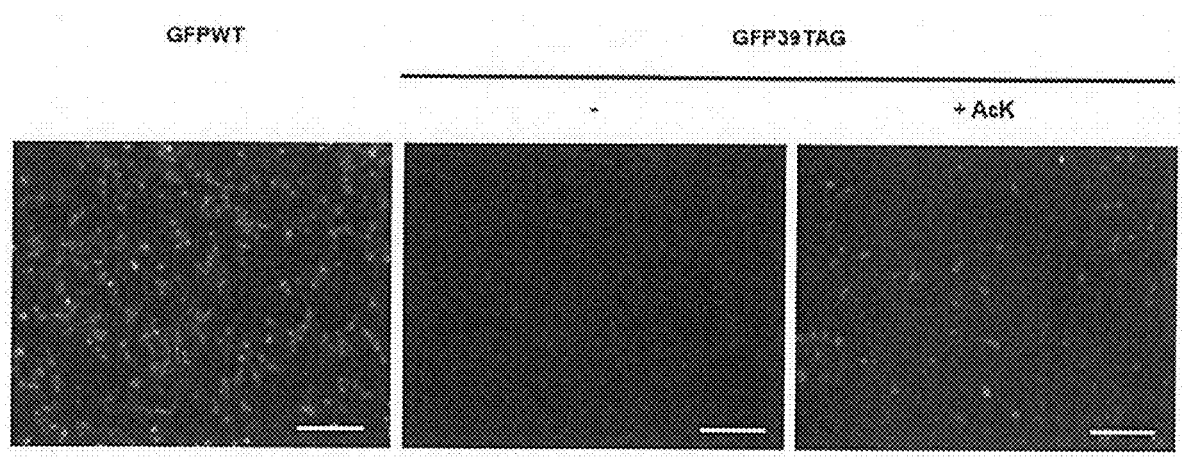
FIG. 3A is a fluorescence image of NIH3T3 cells transfected with the vector of the present invention in the presence or absence of AcK.
Figure 3B:
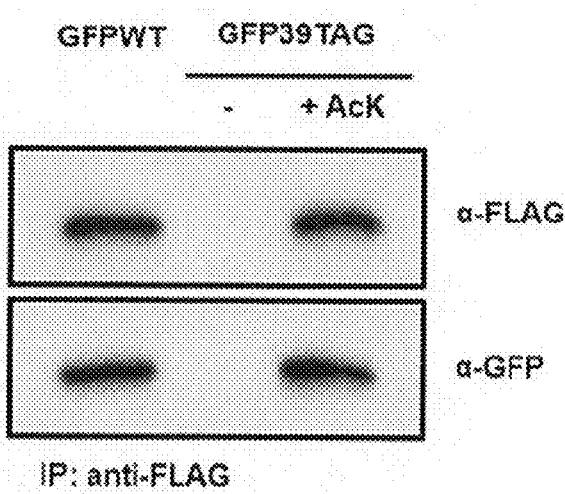
FIG. 3B shows the results of Western blot analysis performed using anti-GFP and anti-FLAG® protein antibodies.
Figure 3C:
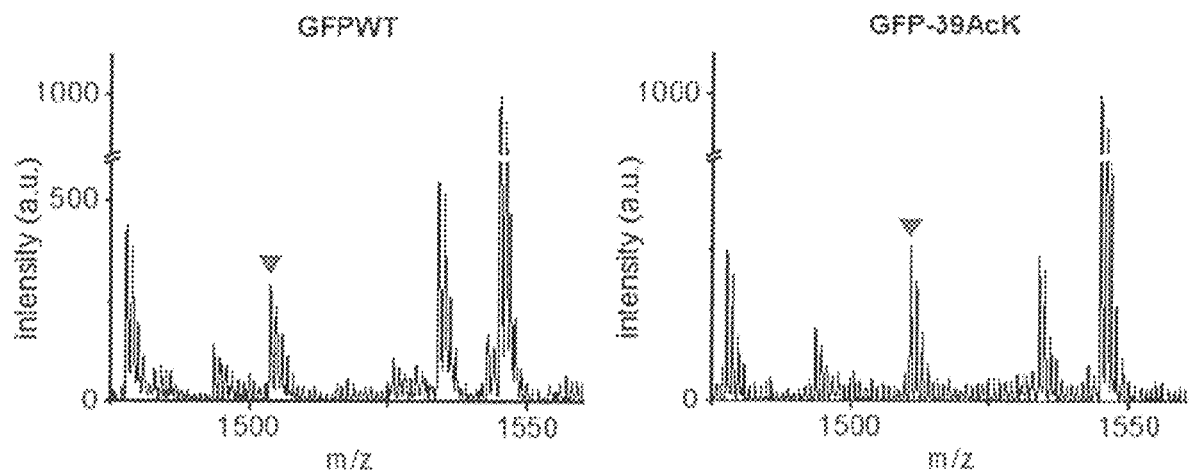
FIG. 3C shows the MALDI-TOF MS analysis of wild-type GFPuv and AcK-incorporated GFPuv after trypsin digestion.

Similarly, NIH3T3 mouse cells, transfected with the two plasmids constructed in Example 1, expressed GFPuv only in the presence of AcK (FIGS. 3A-3C).

Example 3: Generation of Transgenic Mouse

The present inventors generated a transgenic mouse transfected with PylT::HA-AcKRS obtained by linearizing the pAcKRS-tRNA plasmid constructed in Example 1, and a transgenic mouse transfected with PylT::GFP39TAG-FLAG® protein obtained by linearizing the pGFPamber-tRNA plasmid. Specifically, each of the linearized plasmids was microinjected into the fertilized eggs of a C57BL/6J mouse, and the fertilized eggs were transferred into surrogates, after which the surrogates were allowed to give birth, thereby generating transgenic mice. The two transgenic mice were crossed with each other to produce a double heterozygous transgenic mouse (AcK-GFPamber).

Figure 4A:
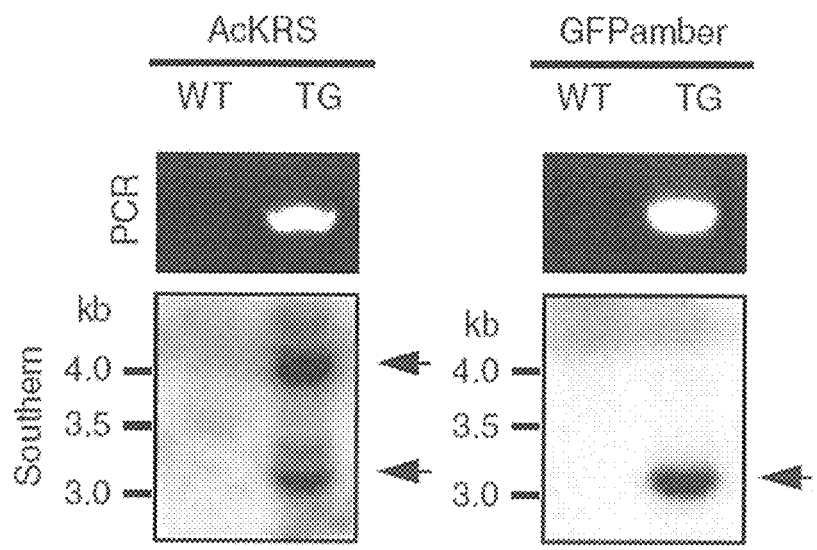
FIG. 4A shows the results of PCR analysis and Southern blotting of AcK-GFPamber double-transgenic mice.
Figure 4B:
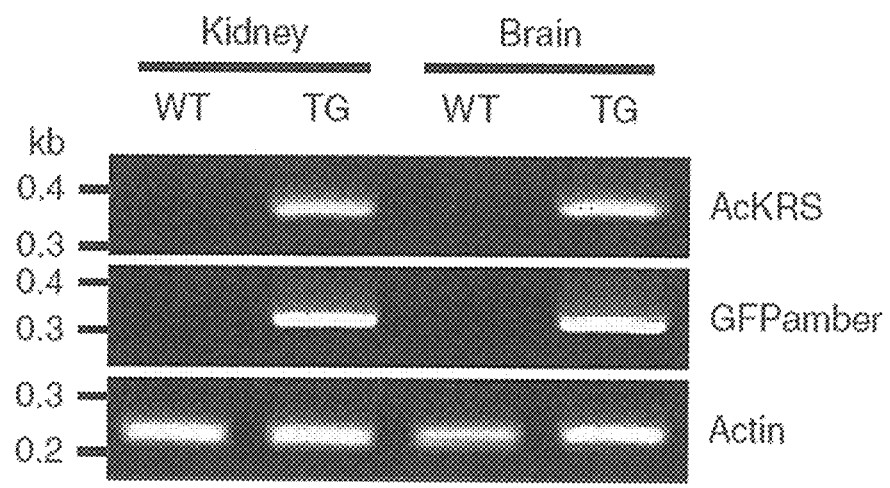
FIG. 4B shows the results of RT-PCR performed using total RNA extracted from the kidney and brain of the transgenic mice.
Figure 4C:
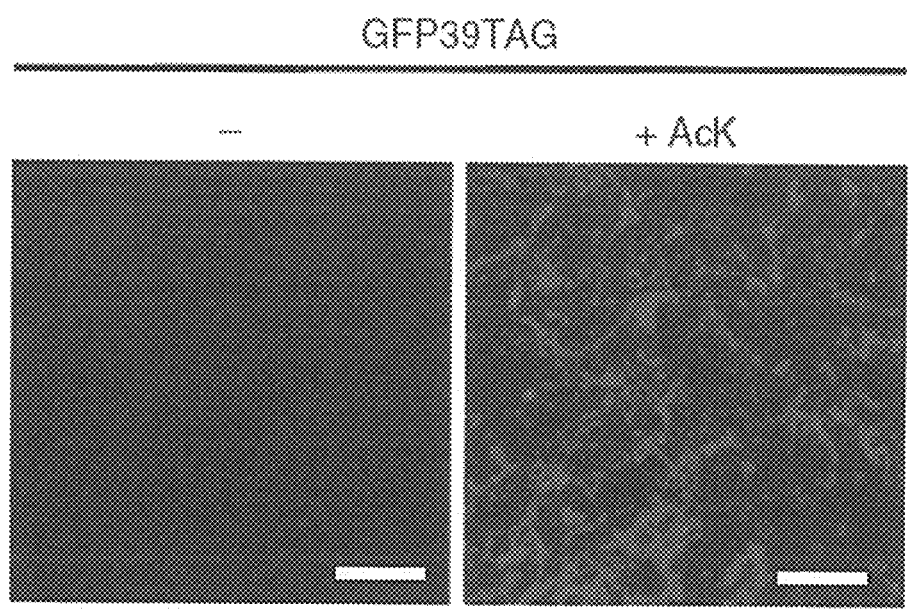
FIG. 4C is a fluorescence image of MEF cells established from AcK-GFPamber mouse (AcKRS/þ, GFPamber/þ) embryos.
Figure 4D:
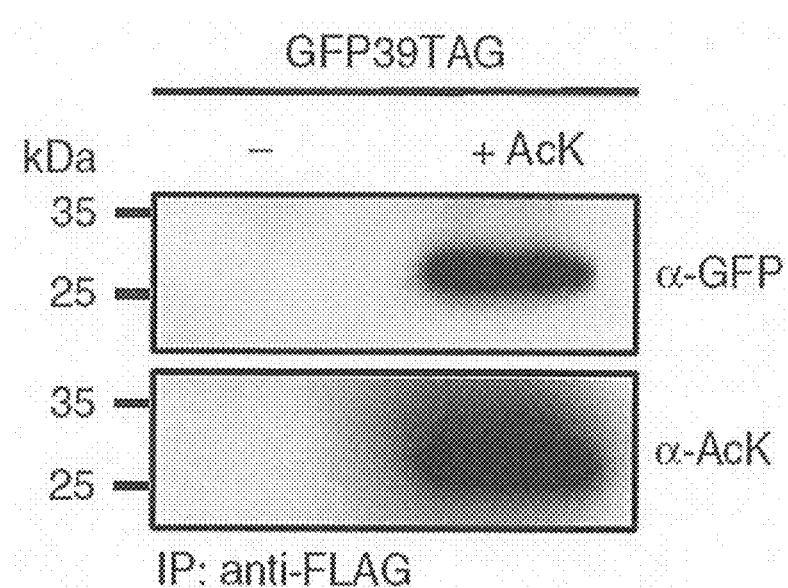
FIG. 4D shows the results of Western blot analysis performed using anti-GFP and anti-AcK antibodies after immunoprecipitation of lysates of the MEF cells with anti-FLAG® protein antibody.
Figure 5A:
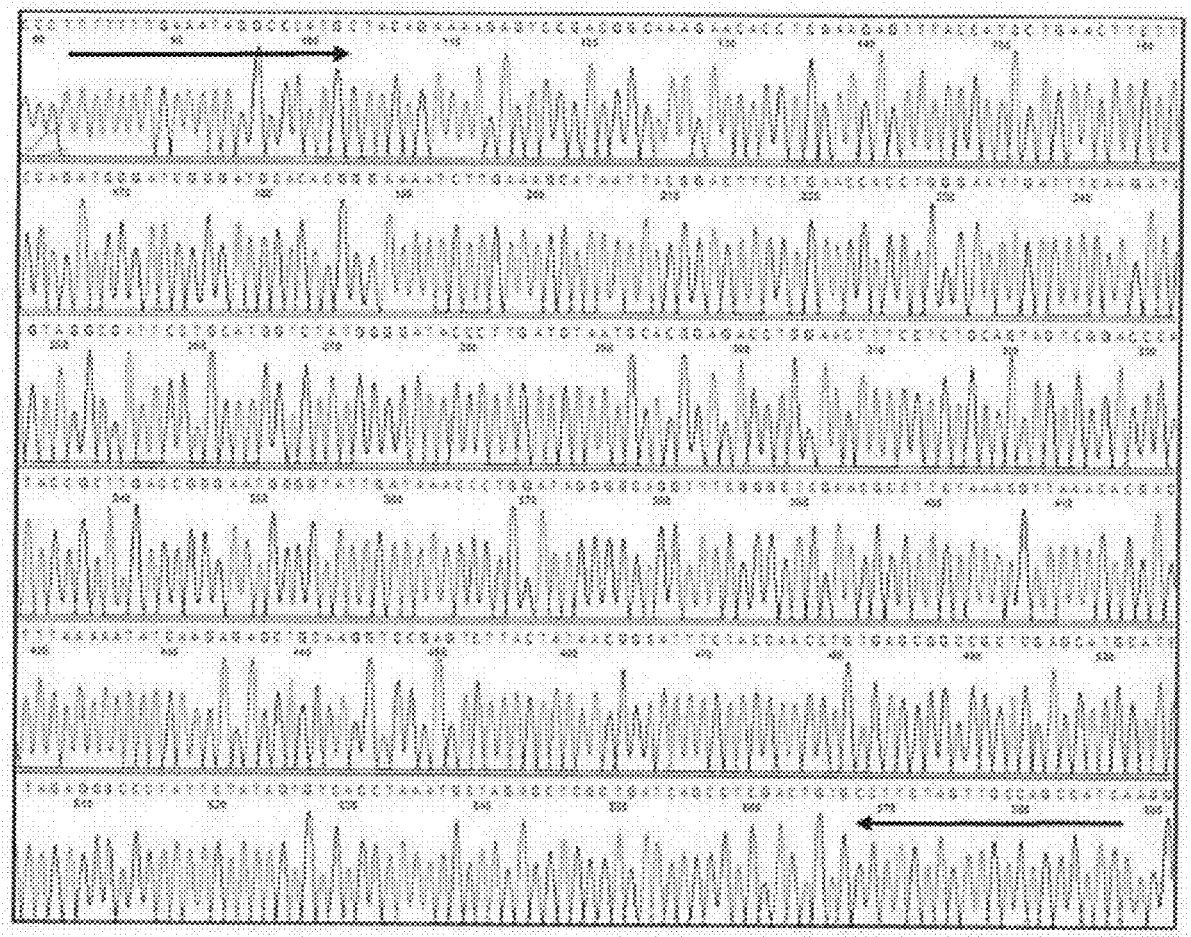
FIGS. 5A-5B show the results of sequencing of genomic DNA extracted from the tail of AcK-GFPamber transgenic mice. Specifically.
Figure 5B:
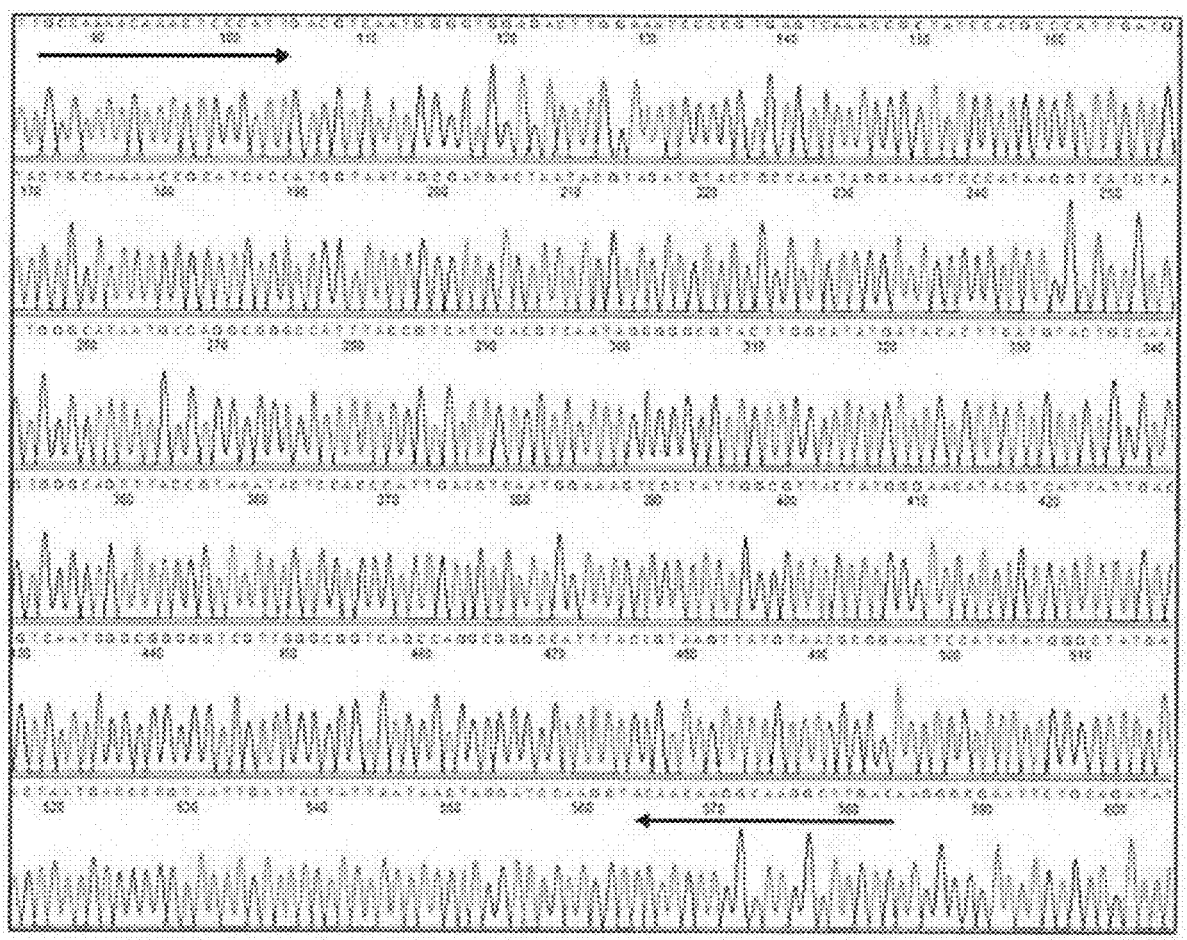

The genotype of the AcK-GFPamber mouse was confirmed by PCR and Southern blot analysis (FIGS. 4A-4D), and stable chromosomal integration of AcKRS and GFPamber transgenes was further confirmed by sequencing of PCR products (FIGS. 5A-5B).

Figure 6:
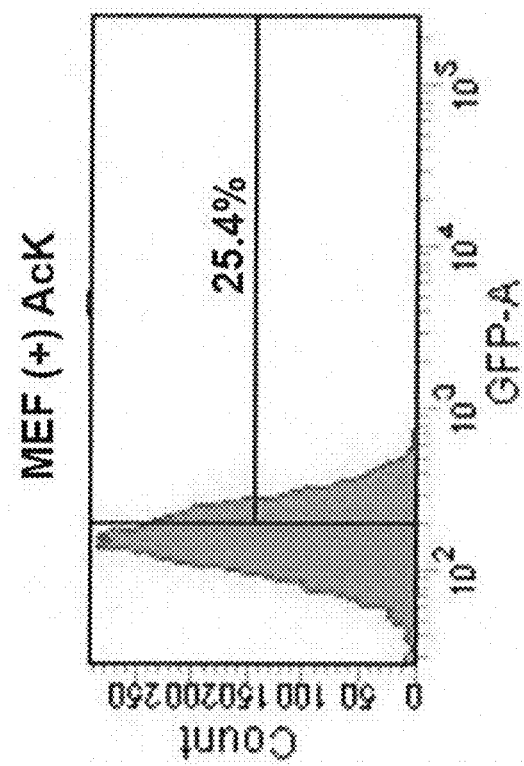
FIG. 6 shows the results of flow cytometric analysis for acetylated GFP expression in MEF cells. The MEF cells were cultured in the presence or absence of 10 mM AcK, and GFPuv expression was analyzed using flow cytometry. GFPuv-positive cells have increased from 4.4% up to 25.4% by the presence of AcK.
Figure 6:
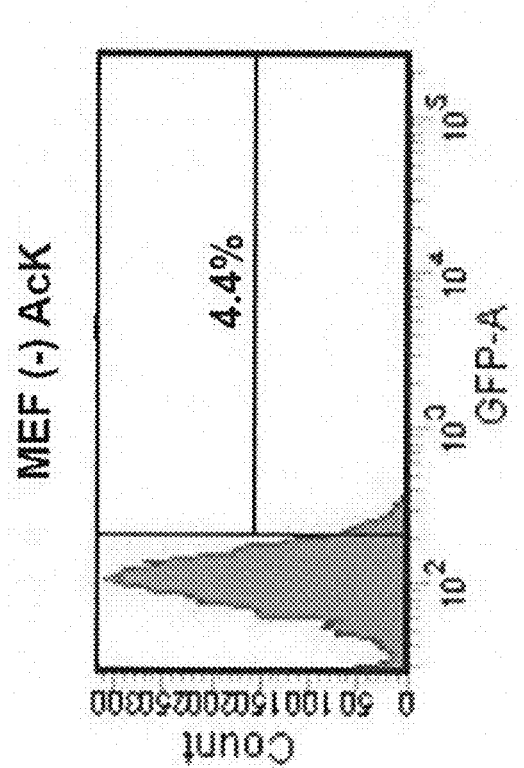

Example 4: Examination of Genetic Incorporation of Unnatural Amino Acid in Mouse Embryonic Fibroblasts Embryonic fibroblasts (MEFs) of the mouse produced in Example 3 were collected and grown, and as a result, it could be seen that fluorescence signals were detected only in the cells grown in the medium containing AcK (FIG. 4C). Also, Western blot analysis of proteins isolated from the MEF cells revealed that these cells expressed GFPuv only in the presence of AcK (FIG. 4D). In addition, flow cytometric analysis indicated that the expression level of the GFPuv protein increased only in the presence of AcK (FIG. 6).

Figure 7A:
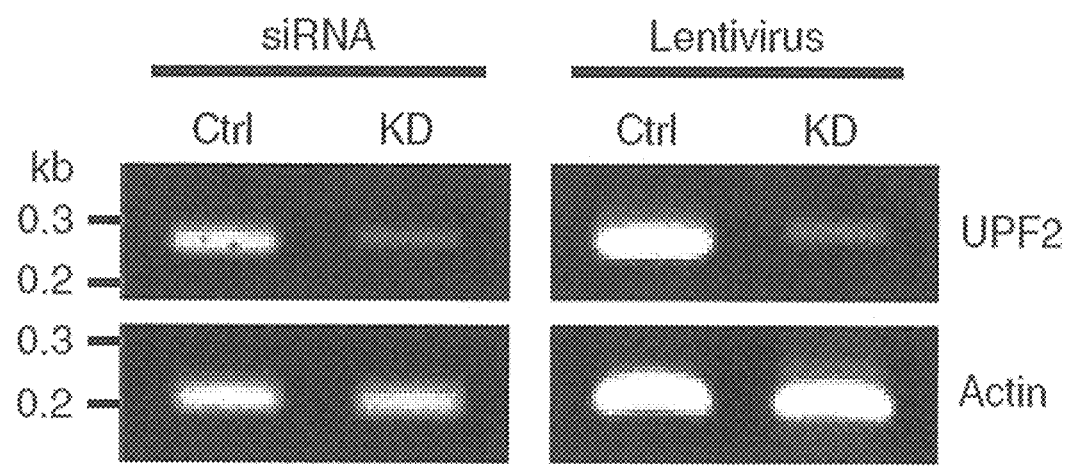
FIG. 7A shows the results of RT-PCR, which indicate that expression of Upf2 in MEF cells was reduced by siRNA or lentivirus.
Figure 7B:
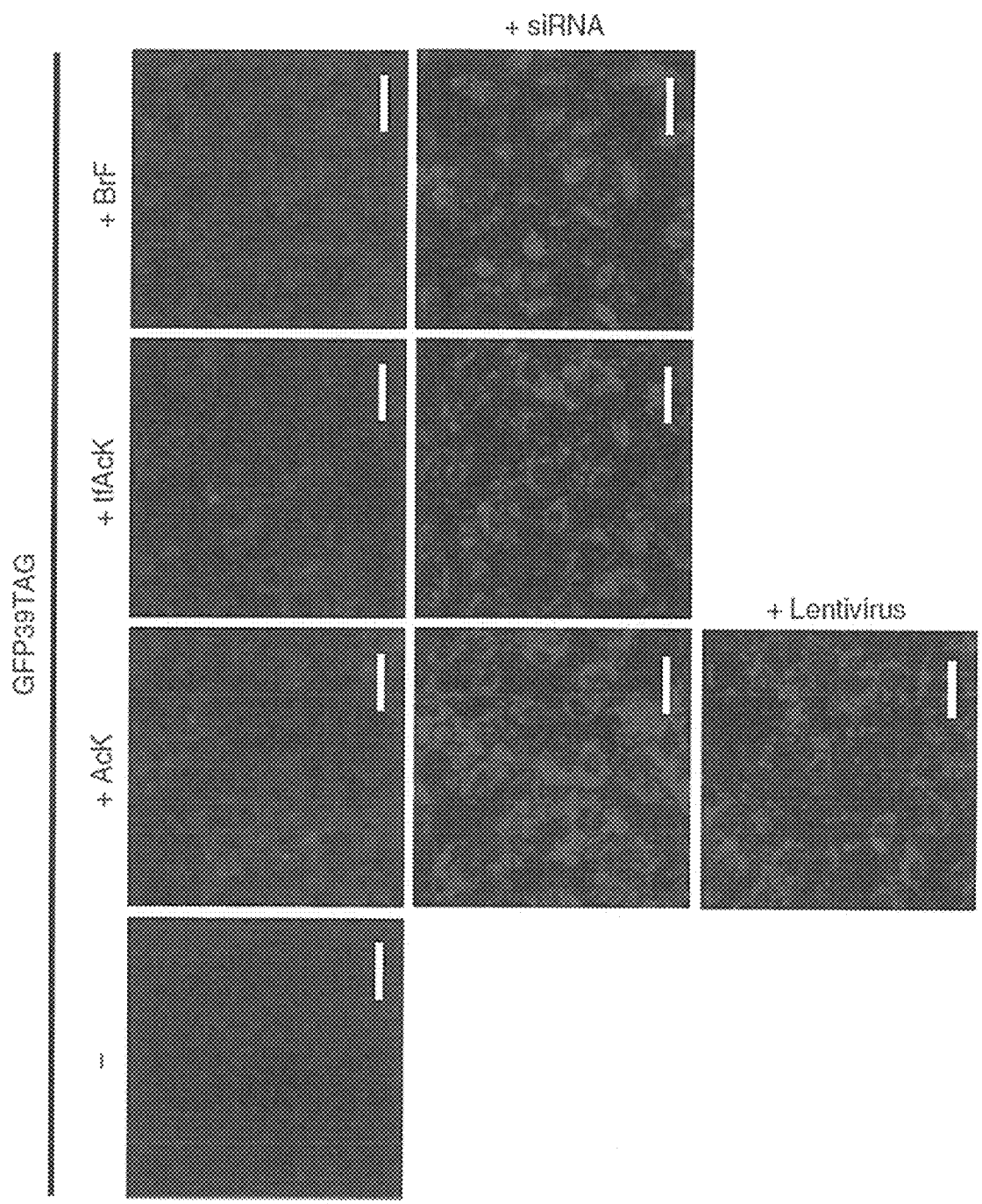
FIG. 7B is a fluorescence image of either MEF cells in which expression of Upf2 was down-regulated using siRNA or lentivirus, or normal MEF cells in the presence of unnatural amino acid (AcK, tfAcK or BrF).

Mammalian cells are known to have a cellular surveillance mechanism known as nonsense mediated-decay (NMD), which degrades mRNAs bearing a premature translation termination codon. Upf2 playing an important role in this NMD system was knocked down using RNA (siRNA) or lentivirus virus specific for Upf2, and as a result, it could be seen that AcK-dependent GFPuv expression in MEF cells increased (FIG. 7B).

Example 5: Examination of Temporal and Spatial Control of Protein Acetylation in Mouse The present inventors examined whether site-specific incorporation of AcK in the AcKRS-GFPamber mouse produced in Example 3 would be possible. For this site-specific incorporation, the mouse should have the ability to express a target protein in a temporally and spatially controllable manner, regardless of cell type and developmental stage.

Figure 8A:
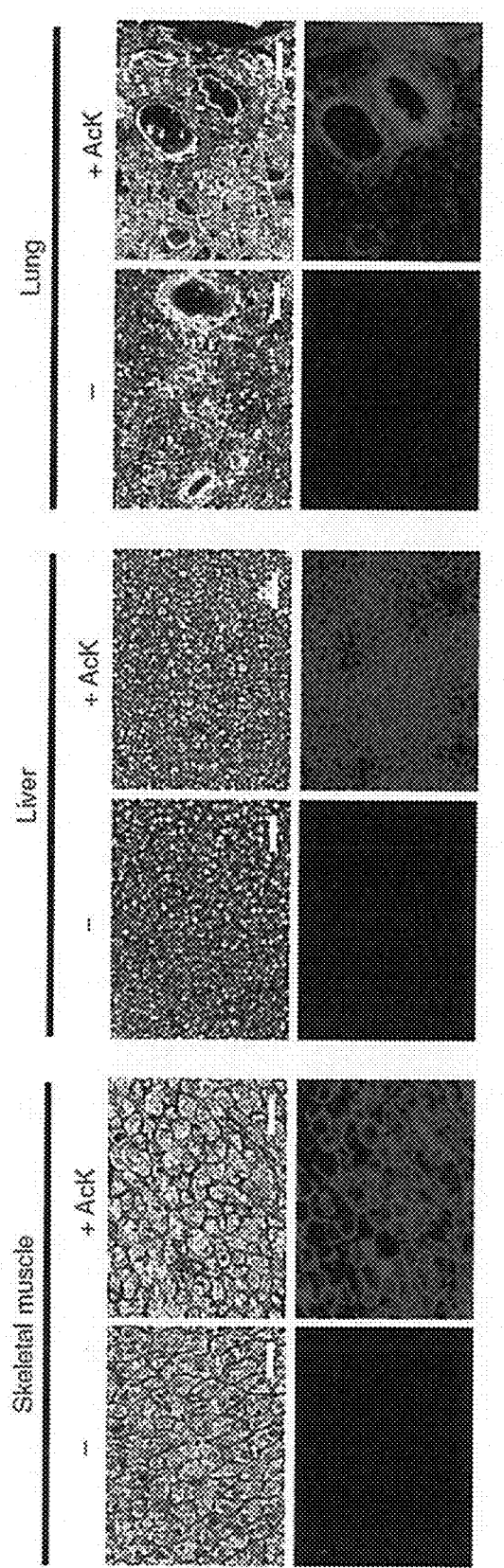
FIG. 8A shows the results of examining temporal expression of acetylated GFPuv in an AcK-GFPamber mouse, which indicate that the expression of GFPuv in skeletal muscle, liver and lung tissues was detected only in the AcK-injected mouse.
Figure 8B:
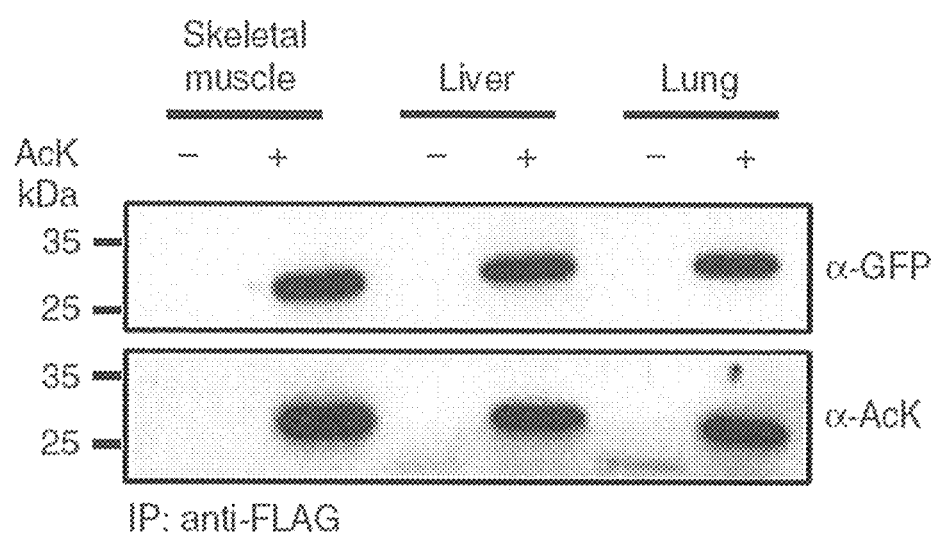
FIG. 8B shows the results of Western blotting of anti-FLAG® protein—immunoprecipitated proteins from tissues of the AcK-GFPamber mouse.
Figure 8C:
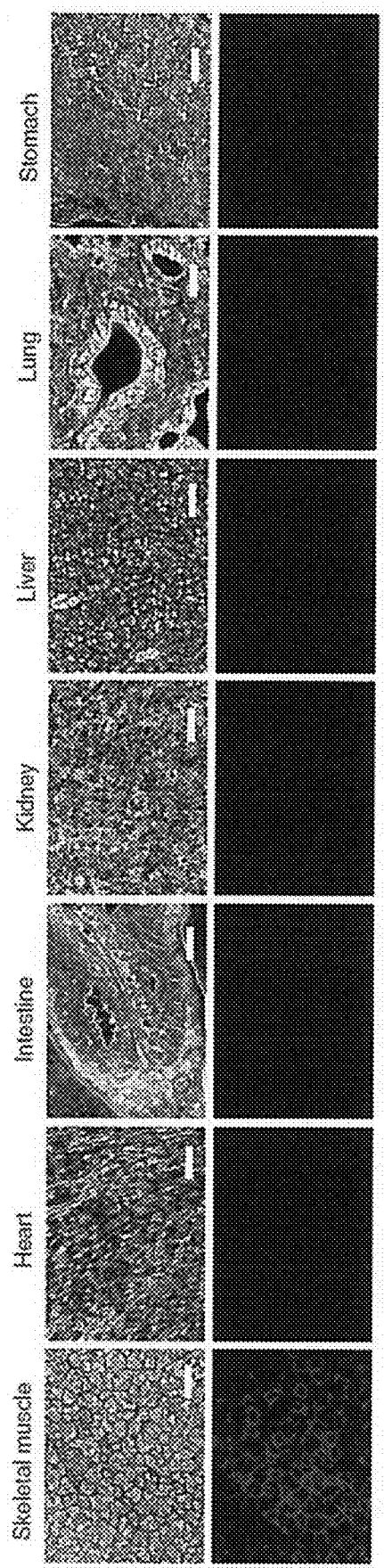
FIG. 8C shows the results of examining spatial expression of acetylated GFPuv in the AcK-GFPamber mouse, and indicates that acetylated GFPuv was observed only in skeletal muscle when AcK was injected into the tissue.
Figure 9:
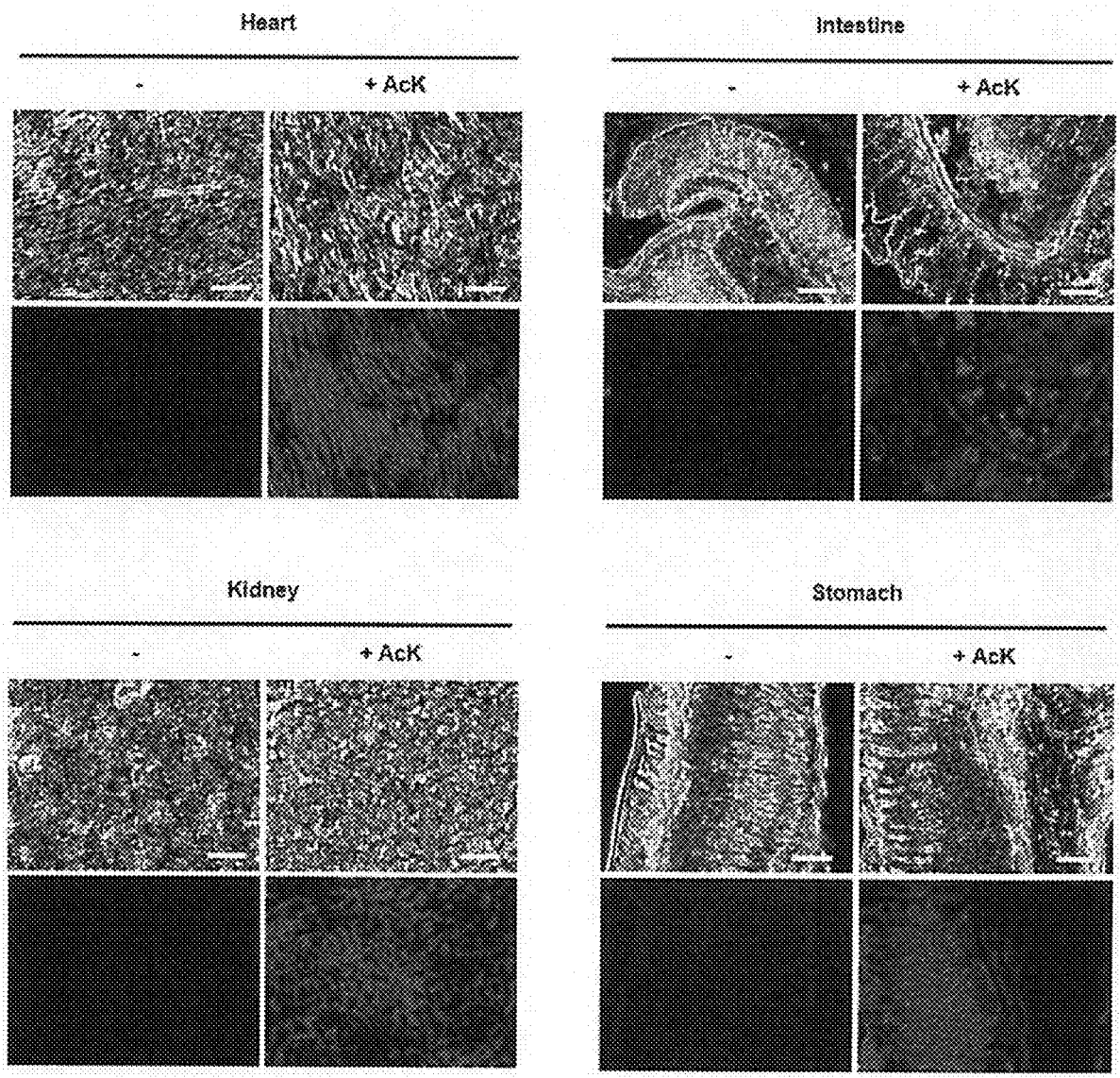
FIG. 9 is a fluorescence image of tissues from AcK-GFPamber double transgenic mouse fed with AcK, and shows that the expression of GFPuv in tissues, heart, intestine, kidney, and stomach was detected only after AcK injection.
Figure 10:
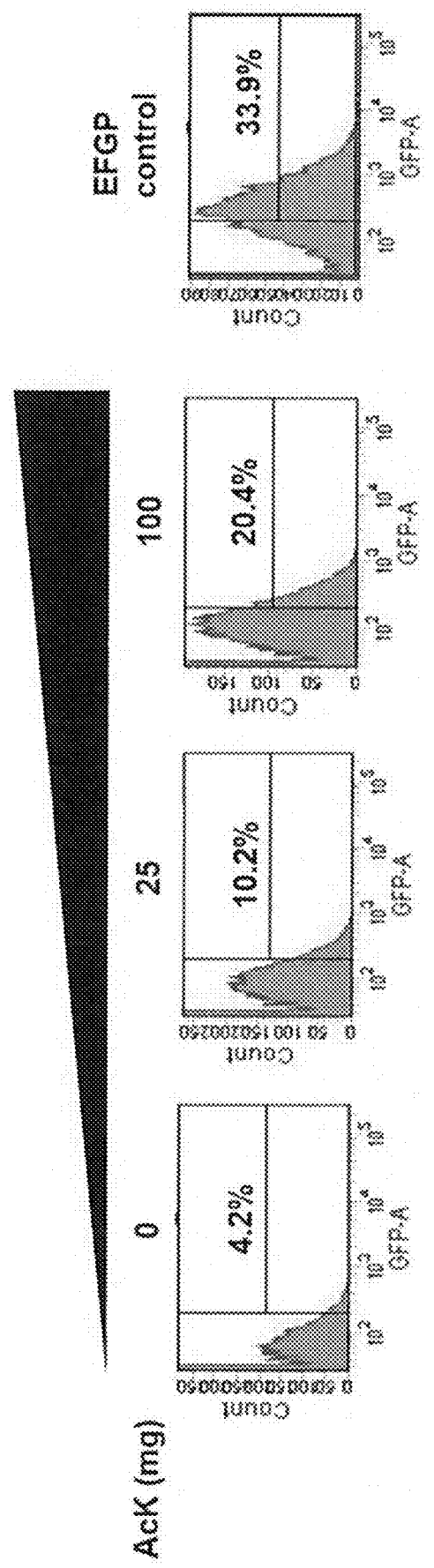
FIG. 10 shows the results of flow cytometric analysis for acetylated GFP expression in liver cells.

Specifically, various samples were collected from a test group injected intraperitoneally with a solution of 50 mg of AcK in PBS daily for 5 days and from a control group injected with PBS alone, and then GFPuv expression was analyzed using a fluorescence microscope. As a result, it could be seen that fluorescence signals were detected only in skeletal muscle, liver and lung tissues from the AcK-injected transgenic mice (FIG. 8A). Furthermore, AcK-dependent GFPuv expression could also be confirmed by Western blot analysis using anti-AcK antibody (FIG. 8B). In addition, GFPuv expression could also be detected in heart, intestine, kidney and stomach (FIG. 9). Moreover, it could be seen that as the amount of AcK increased, the amount of GFPuv also increased (FIG. 10).

Next, the present inventors tested tissue-specific expression of acetylated GFPuv by direct delivery of AcK to the target tissue of the ACKRS-GFPamber mouse. As a result, it could be seen that when AcK was injected directly into the skeletal muscle of the mouse, fluorescence was observed only in the skeletal muscle, and not in other tissues (FIG.

4C). Similarly, it could be seen that when AcK was injected directly into the liver or kidney of the mouse, fluorescence appeared only in the tissue injected with AcK (FIGS. 11A-11B).

Example 6: Examination of Temporal and Spatial Control of Tau Protein Acetylation in Mouse An AcKRS-Tau-amber mouse was produced according to the methods described in Examples 1 to 3, and examination was performed to determine whether Tau protein acetylation resulting from site-specific incorporation of AcK would be possible. To this end, 10 mg of AcK was incorporated onto the head of a 6-week old AcKRS-Tau-amber mouse, and then tissue samples were obtained from the brain, heart, liver and kidney of the mouse and analyzed by Western blot analysis. As a result, it could be seen that acetylated Tau protein was detected only in the brain.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

INDUSTRIAL APPLICABILITY

In the mouse according to the present invention, in which site-specific modification of a target protein is temporally and spatially controllable, expression of the target protein having the site-specific modification attached thereto is controllable depending on the timing and/or position of incorporation of an unnatural amino acid. Thus, the mouse according to the present invention is useful for studies on the in vivo functions of cellular proteins, various human diseases including cancers and neurodegenerative disorders, new drug discovery, and the like.

The invention claimed is:

1. A tRNA synthetase expression vector comprising:
   a human elongation factor 1-α promoter;
   a gene encoding N$^\varepsilon$-acetyl-lysyl-tRNA synthetase (AcKRS), comprising a nucleotide sequence encoding the amino acid sequence of SEQ ID NO: 1;
   a CMV immediately early enhancer;
   an RNA polymerase III promoter U6; and
   a gene encoding tRNA$^{pyl}$.

2. The expression vector of claim 1, wherein the gene encoding tRNA$^{pyl}$ comprises a nucleotide sequence of SEQ ID NO: 2.

3. The expression vector of claim 1, wherein the tRNA synthetase expression vector comprises a nucleotide sequence of SEQ ID NO: 3.

4. A mouse (*Mus Musculus*) having an AcKRS/+ genotype as a result of introduction of the expression vector of claim 1.

5. The mouse of claim 4, further comprising a target protein expression vector carrying an amber codon at a specific position, the expression vector comprising:
   a human elongation factor 1-α promoter;
   a gene encoding a target protein carrying the amber codon at a specific position;
   a CMV immediately early enhancer;
   an RNA polymerase III promoter U6; and
   a gene encoding tRNA$^{pyl}$.

6. The mouse of claim 5, wherein the target protein is a protein incorporated with an unnatural amino acid at a specific position to temporally and spatially control the expression of target protein carrying a site-specific modification.

7. The mouse of claim 6, wherein the unnatural amino acid is selected from the group consisting of N$^\varepsilon$-acetyl-lysine, N$^\varepsilon$-trifluoroacetyl-lysine, and 3-bromo-phenylalanine.

8. A method of using a mouse as claimed in claim 6 to produce a target protein, said method comprising:
   feeding said mouse a feed including an unnatural amino acid; and
   expressing in the mouse the target protein incorporated with the unnatural amino acid, 1 to 5 days after said feeding of feed including the unnatural amino acid.

9. A method of using a mouse as claimed in claim 6 to produce a target protein, said method comprising:
   introducing an unnatural amino acid directly to a desired position or tissue in the mouse; and
   expressing in the mouse the target protein incorporated with the unnatural amino acid.

10. The method of claim 9, wherein the desired position is selected from the group consisting of skin, brain, muscle, intestine, liver, kidney, lung, stomach, and heart.

11. A method for producing a mouse having an AcKRS/+, target protein-amber/+ genotype, the method comprising the steps of:
   (a) linearizing the expression vector of claim 1, microinjecting the linearized expression vector into fertilized mouse eggs, transferring the fertilized eggs into a surrogate, and then allowing the surrogate to give birth, thereby producing a first mouse having an AcKRS/+ genotype;
   (b) linearizing an expression vector comprising a human elongation factor 1-α promoter, a gene encoding a target protein carrying the amber codon at a specific position, a CMV immediately early enhancer, an RNA polymerase III promoter U6, and a gene encoding tRNA$^{pyl}$, microinjecting the linearized expression vector into fertilized mouse eggs, transferring the fertilized eggs into a surrogate, and then allowing the surrogate to give birth, thereby producing a second mouse having a target protein-amber/+ genotype; and
   (c) crossing the first mouse with the second mouse, thereby producing a mouse having an AcKRS/+, target protein-amber/+ genotype.

* * * * *

UNITED STATES PATENT AND TRADEMARK OFFICE
CERTIFICATE OF CORRECTION

PATENT NO. : 10,905,107 B2
APPLICATION NO. : 15/695417
DATED : February 2, 2021
INVENTOR(S) : Hee-Sung Park et al.

Page 1 of 1

It is certified that error appears in the above-identified patent and that said Letters Patent is hereby corrected as shown below:

In the Specification

Column 10, Lines 61-62, "TRITON' X-100" should be -- TRITON™ X-100 --.

Column 10, Line 62, "NP $^{40™}$ detergent" should be -- NP-40™ detergent --.

Column 11, Line 24, "1.5 µd" should be -- 1.5 µl --.

Signed and Sealed this
Eleventh Day of May, 2021

Drew Hirshfeld
*Performing the Functions and Duties of the*
*Under Secretary of Commerce for Intellectual Property and*
*Director of the United States Patent and Trademark Office*